(12) United States Patent
Raskov

(10) Patent No.: US 6,703,380 B2
(45) Date of Patent: Mar. 9, 2004

(54) PREVENTION OF CANCER

(75) Inventor: Hans Henrik Raskov, Kildegårdsvej 31a, DK-2900 Hellerup (DK)

(73) Assignees: Colotech A/S, Kobenhavn K (DK); Hans Henrik Raskov, Frederiksberg C (DK)

(*) Notice: Subject to any disclaimer, the term of this patent is extended or adjusted under 35 U.S.C. 154(b) by 0 days.

(21) Appl. No.: 09/825,891

(22) Filed: Apr. 5, 2001

(65) Prior Publication Data

US 2001/0049364 A1 Dec. 6, 2001

Related U.S. Application Data

(63) Continuation-in-part of application No. PCT/DK00/00546, filed on Sep. 29, 2000.

(30) Foreign Application Priority Data

Sep. 29, 1999 (DK) .......................................... 1999 01390

(51) Int. Cl.[7] .......................... A61K 31/60; A61K 31/69
(52) U.S. Cl. ...................................... 514/165; 514/167
(58) Field of Search ................................. 514/167, 165

(56) References Cited

FOREIGN PATENT DOCUMENTS

| DE | 43 34 154 | 4/1995 |
|----|-----------|--------|
| EP | 0 205 025 | 12/1986 |
| EP | 0 412 110 | 7/1993 |
| WO | WO 89/10351 | 11/1989 |
| WO | WO 93/09093 | 5/1993 |
| WO | WO 93/19044 | 9/1993 |
| WO | WO 94/14766 | 7/1994 |
| WO | WO 94/26707 | 11/1994 |
| WO | WO 95/02577 | 1/1995 |
| WO | WO 95/03273 | 2/1995 |
| WO | WO 96/41645 | 12/1996 |

OTHER PUBLICATIONS

Meggouh et al., J. Steroid Biochem., (1990) vol. 36, No. 1–2, pp. 143–147 Abstract Only.*
Walter T. Boone, Scientific Article, Journal MSMA, "Colorectal Cancer–Chemoprevention", pp. 318–322 (Sep. 1998).
Trujillo, M. A. et al., Dig. Dis. Sci. 39:2260–2266 (1994), "Non–steroidal antiinlfammatory agents in chemoprevention of colorectal cancer. At what cost?".
Caplan, L. S. et al., Curr. Opin. Oncol. 8:441–446 (1996), "Secondary prevention of cancer".
Key, Jak et al., BMJ 313:775–779 (1996), "Dietary habits and mortality in 11000 vegetarians and health conscious people: results of a 17 year follow–up".
Garland, C. F. et al., Lancet 307–309 (1985), "Dietary vitamin D and calcium and risk of colorectal cancer: a 19–year prospective study in men".
Garland, C. F. et al., Lancet 18:1176–1178 (1989), "Serum 25 hydroxyvitamin D and colon cancer: eight–year prospective study".

Garland, C. F. et al., Am. J. Clin. Nutr. 54:193S–201S (1991), "Can colon cancer incidence and death rates be reduced with calcium and vitamin D?".
Kune, G. A. et al., "Colorectal cancer risk, chronic illnesses, operations and medications: case control results from the Melbourne Colorectal Cancer Study", (1988) Cancer Res. 48:4399–4404.
Suh, O. et al., Cancer 72:1171–1177 (1993), "Aspirin use, cancer and polyps of the large bowel".
Thun, M. J. et al., "Aspirin use and reduced risk of fatal colon cancer", 1991 N. Engl. J. Med. 325:1593–1596.
Buring, J. E. et al., "Nonsteroidal antiinflammatory drugs and colorectal cancer", 1994 Cancer 74:1837–1839.
Heath, C. W. et al., "Nonsteroidal antiinflammatory and human cancer", 1994 Cancer 74:2885–2888.
Pence, BC., "Role of calcium in colon cancer prevention: experimental and clinical studies", 1993 Mut Res 290:87–95.
Duris, I. et al., "Calcium chemoprevention in colorectal cancer", 1996 Hepatogastro–enterol 43:152–154.
Buset, M. et al., "Inhibition of human colonic epithelial cell proliferation in vivo and in vitro by calcium" 1986 Cancer Res. 46:5426–5430.
Wargovich, M. J. et al., "Calcium and vitamin D modulate mouse colon epithelial proliferation and growth characteristics of a human colon tumor cell line", 1987 Can J. Physiol Pharmacol 65:472–477.
Dorudi, S. et al., "Levels of expression of E–cadherin m–RNA in colorectal cancer correlates with clinical outcome", 1995 Br. J. Cancer 71:614–616.
Newmark, H. L. et al., "Calcium, vitamin D and colon cancer", 1992 Cancer Research 52:20067S–2070S.
Rasmussen, H., "The calcium messenger system", 1986 N. Engl. J. Med 314:1094–1101.
Llor, X et al., "K–ras mutations in 1,2 dimethylhydrazine induced colonic tumors: effects of supplemental diatary calcium and vitamin D deficiency", 1991 Cancer Res. 51. 4305–4309.
Reshef, R. et al., "Effect of a calcium enriched diet on the colonic epithelial hyperproliferation induced by N–methyl–N–nitro–N–nitrosoguanidine in rats on a low calcium and fat diet", 1990 Cancer Res. 50:1764–1767.

(List continued on next page.)

Primary Examiner—Jerome D. Goldberg
(74) Attorney, Agent, or Firm—Hunton & Williams LLP

(57) ABSTRACT

The present invention relates to a method for the prevention of cancer or the initiation and/or progression of cancer in a human comprising administration to the human a combination dosage of a cyclooxygenase (COX) inhibitor, a vitamin $D_3$ including analogues and metabolites thereof and calcium. In a further embodiment the invention relates to the use of the combination dosage for the preparation of a medicament and to such pharmaceutical preparations. In a further aspect the invention relates to a method for reducing the effective dosage of ASA in a chemoprofylactive treatment of colorectal cancer in a human by co-administration with a non toxic dosage of a vitamin $D_3$ including analogues and metabolites thereof and Ca in the form of a combination dosage.

13 Claims, No Drawings

OTHER PUBLICATIONS

Kane, K. F. et al., "Functional vitamin D3 receptors are present in human colorectal neoplasms", 1995 Gastroenterology 108:A487.

Cross, H. S. et al., "Vitamin D receptor and cytokeratin expression may be expression indicators in human colon cancer", 1996 Anticancer Res. 16:2333–2338.

Eisman, J. A. et al., "Suppression of in vivo growth of human cancer solid xenografts by 1,25-dihydroxyvitamin D3", 1987 Cancer Res. 47:21–25.

Ternent, C. et al., "Lipoxygenase blockade inhibits growth factor–induced colonic cancer cell proliferation", 1999 Abstract, ASCRS Ann. Meeting 1999.

Marcus, A. J., "Aspirin as prophylaxis against colorectal cancer", 1995 N Engl. J. Med. 333:656–658.

Frolich, J. C., "A classification of NSAIDs according to the relative inhibition of cyclooxygenase enzymes", 1997 TIPS 18: 30–34.

Hanif, A. P. et al., "NSAIDs inhibit the growth of colon cancer cell lines by a prostaflandin independant pathway", 1995 Gastroente-rology 108:A478.

Ahnen, D. et al., "Sulindac sulfide and sulfone both inhibit the growth of colon cancer cell lines by inducing apoptosis", 1995 Gastroente-rology 108:A443.

Alberts, D. S. et al., "Do NSAIDs exert their colon cancer chemoprevention activities through the inhibition of mucosal prostaglandin synthetase?", 1995 J. Cell Biochem s22: 18–23.

Kahlenberg, M. et al., "Nonsteroidal antiinflammatory drugs (NSAID's) reduce genomic instability in colorectal tumor cells", 1998 Abstract. Surgical Oncology Societies 51st Annual Cancer Symposium 1998.

Levy, G., "Prostataglandin H synthases, nonsteroidal antiinflammatory drugs and colon cancer", 1997 FASEB J. 11:234–247.

Hixson, L. J. et al., "Antiproliferative effect of non–steroidal antiinflammatory drugs against human colon cancer cells", 1994 Cancer Epidemiol Biomarkers Prev. 3:5:433–438.

Dubois, R. N. et al, "Nonsteroidal antiinflammatory drugs, eicosanoids and colorectal cancer prevention", 1996 Gastroenterol Clin. N. Am. 25:773–791.

Watson, A J., "Chemopreventive effects of NSAIDs against colorectal cancer:regulation of apoptosis and mitosis by COX–1 and COS–2", 1998 Histol Histopathol 13:591–597.

Steering Committee of the Physicians Health Study Research Group, "Final report on the aspirin component of the ongoing Physician Health Study", 1989 N. Engl. J. Med. 321:129–135.

Muscat, J. E. et al., "Nonsteroidal Antiinflammatory drugs and colorectal cancer", 1994 Cancer 74:1847–1854.

Giovannucci, E. et al., "Aspirin and the risk of colorectal cancer in women", 1995 N. Engl. J. Med. 333:609–614.

Giovannucci, E. et al., "Aspirin use the risk of colorectal cancer and adenoma in male health professionals", 1994 Ann. Int. Med. 121:241–246.

Pollard, M. et al., "Effect of indomethacin on intestinal tumors induced in rats by the acetate derivative of dimethylnitrosamine", 1981 Science 214:558–559.

Reddy, B. S. et al., "Dose–related inhibition of colon carcinogenesis by dietary piroxidam, a nonsteroidal antiinflammatory drug, during different stages of rat colon tumor development", 1987 Cancer Res. 47:5340–5346.

Narisawa, T. et al., "Inhibition of development of methylnitrosurea induced rat colon tumors by indomethacin treatment", 1981 Cancer Res. 41:1954–1957.

Kudo, T. et al., "Antitumor activiy of indomethacin on methylazoxymethanol–induced large bowel tumors in rats", 1980 Gann. 71:260–264.

Caprie Steering Committee, "A randomised, blinded, trial of clopidogrel versus aspirin in patients at risk of ischaemic events (CAPRIE)" 1996 Lancet 348:1329–1339.

Dwerryhouse, S. J. et al., "Non–cytotoxic control of colorectal cancer", 1997 Royal College of Surgeons of Edinburgh 141–153.

Sokoloski, John A. and Sartorelli, Alan C., "Induction of the differentiation of HL–60 promyelocytic leukemia cells by nonsteroidal anti–inflammatory agents in combination with low levels of vitamin $D_3$", 1998 Leukemia Research 2:153–161.

Pence, Barbara C. et al., "Chemopreventive effects of calcium but not aspirin supplementation in cholic acid–promoted colon carcinogenesis: correlation with intermediate endpoints", 1995 Carcinogenisis 4:757–765.

Kristiansen, E., et al., "Influence of different diets on development of DMH–induced aberrant crypt foci and colon tumor incidence in Wistar rats", 1995 Nutr. Cancer 23, 151–159.

Díaz, Darío, et al., "Apoptosis is induced by the active metabolite of vitamin $D_3$ and its analogue EB1089 in colorectal adenoma and carcinoma cells :possible implications for prevention and therapy", 2000 Cancer research 60, 2304–2312.

Tsujiuchi T., et al., "Mutations of ademonatous polyposis coli and beta–catenin genes during progression of lung tumours induced by N–nitrosobis (2–hydroxypropyl) amine in rats", 2000 Cancer Res. 60:6611–6.

Sunaga, N., et al., "Constitutive activation of the Wnt signalling pathway by CTNNB1 (beta–catenin) mutations in a subset of human lung adenocarcinoma.", 2001 Genes Chromosomes Cancer 30:316–321.

Piyathilake, C.J. et al., "Localized folate and vitamin B–12 deficienty in squamous cell lung cancer is associated with global DNA hypomethylation", 2000 Nutr. Cancer 37:99–107.

Hirsch, F. R. et al., "Early detection of lung cancer: clinical perspectives of recent advances in biology and radiology", 2001 Clin. Cancer Res. 7:5–22.

Saha, D. et al., "Synergistic induction of cyclooxygenase–2 by transforming growth factor–beta1 and epidermal growth factor inhibits apoptosis in epithellal cells", 1999 Neoplasia1 508–517.

Kim, T. et al., "Alteration of cell growth and morphology by overexpression of transforming growth factor beta type II receptor in human lung adenocarcinoma cells", 2001 Lung cancer 31:181–191.

Marrogi, A. J. et al., "Nitric oxide synthase, cyclooxygenase 2 and vascular endothelial growth factor in the angiogenesis of non–small cell lung carcinoma", 2000 Clin. Cancer Res. 6:4739–4744.

Hosomi, Y. et al., "Increased cyclooxygenase 2(COX–2) expression occurs frequently in precursor lesions of human adenocarcinoma of the lung", 2000 Lung Cancer 30:73–81.

Shirharama, T., "Cyclooxygenase–2 expression is up–regulated in transitional cell carcinoma and its preneoplastic lesions in the human urinary bladder", 2000 Clin. Cancer Res. 6:2424–2430.

Ristimaki, A. et al., "Expression of cyclooxygenase–2 in human transitional cell carcinoma of the urinary bladder", 2001 Am. J. Pathol 158:849–853.

Rioux, N. et al., "The induction of cyclooxygenase–1 by a tobacco carcinogen in U937 human macrophages is correlated to the activation of NF–kB", 2000 Carcinogenesis 21:1745–1751.

Witschi, H. et al., "Chemoprevention of tobacco–smoke lung carcinogenesis in mice after cessation of smoke exposure", 2000 Carcinogenesis 21:977–982.

Montoya, R. G. et al., "Chemoprevention of gatrointestinal cancer", 1997 Cancer and Metastasis Reviews 16:405–419.

Pence, B. C. et al., "Experimental chemoprevention of colon carcinogenesis by combined calcium and aspirin", 1994 Proceedings of the American Association for Cancer Research 35:624.

Niv, Y. et al., "In Colorectal Carcinoma Patients, Serum Vitamin D levels vary according to stage of the carcinoma", 1999 Cancer 86:391–397.

Kahn, M. et al., "Chemoprevention for colorectal carcinoma", 1997 Hematol. Oncol. Clin. North Am. 11:779–794.

* cited by examiner

PREVENTION OF CANCER

The present application is a continuation-in-part application of international patent application no. PCT/DK00/00546 filed on Sep. 29, 2000. This patent application as well as all documents cited in the text of this application are hereby incorporated herein by reference.

The present invention relates to the chemoprophylaxis of colorectal cancer with combinations of a cyclooxygenase (COX) inhibitor, vitamin $D_3$ including analogues and metabolites thereof and/or calcium. In a further aspect the invention relates to a method for reducing the effective dosage of ASA in a chemoprofylactive treatment of colorectal cancer in a human by co-administration with a non toxic dosage of a vitamin $D_3$ including analogues and metabolites thereof and Ca in the form of a combination dosage. In a still further embodiment the invention relates to the use of a cyclooxygenase (COX) inhibitor, a vitamin $D_3$ and calcium together with a pharmaceutically acceptable carrier for the preparation of a medicament for preventing the initiation and/or progression of colorectal cancer in a human. The invention also relates to such a pharmaceutical medicament.

Colorectal cancer (CRC) is one of the leading cancer forms in the Western world (1.3 million per year and over 600,000 annual deaths). In Denmark, the incidence is approximately 65 per 100,000 inhabitants and correlates to age. Concurrently with a fall in tobacco smoking in Western industrial countries and an increased life expectancy, CRC is expected to become the most frequent solid cancer over the next decades.

The great majority of CRC cases are sporadic cancers, for which it is not possible to establish a genetic disposition. Effective CRC prevention in well-defined risk groups would have a significant effect on population health.

In the average population the lifetime risk of getting CRC is 6 per cent, and the risk of dying from the disease is 3 per cent (1,2,3). In first-degree relatives of patients with CRC, the risk is several times higher. In rare cases, the CRC disposing factors are hereditary non-polyposis colorectal cancer (HNPCC), where it is possible to establish the presence of mutations in mismatch repair genes, familial adenomatous polyposis (FAP, mutation in the APC gene), or inflammatory bowel diseases (ulcerative colitis and Crohn's disease), these factors accounting for 5 to 15 per cent in all.

There is no doubt that foods are the most important causal factor, including animal proteins and fats, which the Western world is increasingly eating in excess amounts instead of cereals, fruits and vegetables. The incidence of CRC is increasing, but it is only half the magnitude among vegetarians as among meat-eaters (4). The progress made during the last decades within surgical techniques, adjuvant treatment, etc, has not lowered mortality to any mentionable degree. CRC screening means tracing cancers at an early stage and removing intestinal polyps, but so far, however, studies have not shown screening to reduce the incidence. The overall five-year survival in Denmark is approximately 30 per cent and depends on the stage at the time of diagnosis. Approximately 25 per cent of the patients have disseminated cancer at the time of diagnosis and are beyond a cure. Three fourths of CRC patients undergo surgery intended to cure; nevertheless, 50 per cent of these patients die within five years because of recurrence.

With the choices and results of treatment known today, only effective prophylaxis will be able to reduce CRC morbidity and mortality (3,5) in a decisive manner.

In recent years, focus is very much on cancer prophylaxis, in acknowledgement of the fact that surgery mostly does not suffice as the only modality and that most cytotoxic regimens are ineffective against solid tumours.

The term chemoprophylaxis covers the use of pharmacologically active, non-cytotoxic agents or naturally occurring nutrients that protect against the emergence and development of clones of mutated, malignant cells.

In 1994, to analyse existing data and to initiate new studies, the National Cancer Institute, USA, established a Chemopreventive Branch. The NCI-CB has concluded that CRC is an attractive target for cancer chemoprophylaxis, since it is a frequent cancer with a high mortality. However, no acceptable treatment is available.

A well-defined multistage carcinogenesis has been mapped with well-defined precursors in the form of colorectal adenomas, and the groups at risk are also well defined.

Some studies have pointed to an inverted correlation between the individual intake of non-steroid anti-inflammatory drugs (NSAID), and of calcium and vitamin $D_3$ and the risk of developing CRC. The studies in question are animal experimental models of colorectal carcinogenesis, prospective studies of patients with FAP and epidemiological studies taking the form of retrospective case-control studies and prospective cohort and interventional studies (6–17). In conclusion, 21 of 23 epidemiological studies have shown that regular use of NSAIDs reduces the risk of CRC by up to 50 per cent (18). However, data are not clear regarding dosage and duration of use. The most frequently studied drugs are acetylsalicylic acid, sulindac, piroxicam and indomethacin.

A few review articles and editorials have been published which find the results interesting, but existing data have neither led to any recommendations proper nor proved any clinical significance (12). This is primarily because of the well-known undesirable effects of NSAIDs and the acknowledgement that the strongest evidence of the effect of these agents does not exist, ie, prospective, randomised double-blind trials in human populations.

The American Cancer Society has concluded that current data from epidemiological, clinical, pharmacological and toxicological studies show that acetylsalicylic acid protects against CRC development (13), and the FDA is currently assessing whether acetylsalicylic acid taken alone should be approved as chemoprophylaxis of CRC, or whether further phase III studies will be necessary.

Animal experimental data draw a promising picture of pharmacologically active drugs that, with different mechanisms of action, appear to be effective chemoprophylactic agents. However, individual epidemiological studies of calcium and vitamin D (or milk products) in relation to CRC are inconsistent. Out of 13 studies of calcium (nine case-control and four cohort studies), eight show a significant inverse correlation, three studies report insignificant correlation, whereas two fail to show any correlation.

Out of five epidemiological studies (three cohort studies and two case-control studies) of the impact of vitamin D on the CRC risk, two show a significant inverse correlation, whereas the rest have no significance.

The sequence of epithelium-adenoma-carcinoma is a process taking many years (5 to 10 years). CRC differs from many other cancers in as much as mutations in cell-cycle regulating genes and gene products are rarely seen. CRC is characterised by mutations in critical tumour suppressor genes (APC, DCC, p53, MCC) and oncogenes (K-ras) and upregulation in growth factors (especially the EGF-family) and enzymatic activity (especially cyclooxygenase).

In spite of CRC being a frequent cancer form, its incidence is only 65 per 100,000 inhabitants, and a clinicalcontrolled study with the endpoints being invasive cancer and cancer-related deaths would require enrolment of tens of thousands individuals, and it would run for several decades and require astronomical financial resources. Healthy individuals do not feel impelled to participate in scientific studies including long-term medicine intake, and the results of any such studies would be subject to confounding.

Over 95 per cent of CRC develop from adenomas, which are accepted CRC precursors in scientific studies of humans and in animal experiments. Other biomarkers include genomic changes (mutations, etc), aberrant crypt foci (ACF), ornithine decarboxylase activity, cyclooxygenase activity and the prostaglandin level in mucosa, which are used as intermediary endpoints.

Colorectal carcinogenesis and Calcium:

In the Western world, the daily average intake of calcium is substantially below the recommended dietary allowance (RDA) of 800 to 1200 mg/day, increasing to 1500 mg/day for the elderly. In Western countries, each adult has an average daily intake of 750 to 850 mg of calcium (14).

Approximately 30 per cent of dietary calcium is absorbed from the intestinal canal, and vitamin $D_3$ stimulates the absorption. The absorption is both transcellular (at low dietary calcium content) and paracellular. The residual amount of calcium in the intestinal lumen binds free fatty acids and secondary bile acids by formation of insoluble soaps and reduces the local irritant effect of these acids in the colon.

Deoxycholic acid (DCA) in particular, which produces epitheliolysis in the epithelial surface of the colon, is considered to be the most carcinogenic and mitogenic of the secondary bile acids (15). Epitheliolysis induces potent proliferation in the crypts, probably as a result of exposure of the basal membrane. In the activated phase (S phase), the cells are more sensitive towards carcinogens like DCA, free fatty acids, etc (16). In vivo the harmful effect of 5 mM DCA can be prevented by increasing the Ca concentration in the intestinal lumen from 0 to 4 mM.

In several cases, the results of case-control studies and cohort studies have shown a significant correlation between a high dietary calcium level and a reduction in the risk of CRC development. However, the results are not unambiguous, although large volumes of data from animal experimental studies all point in the same direction (14). One prospective study shows a significant reduction in the rate of polyp recurrence and a significant increase in cancer-related survival following CRC surgery at calcium supplements (calcium carbonate 2 g/day (17).

The formation of insoluble calcium soaps is still considered to be the most important mechanism of the cancer preventive action of calcium, but in recent years focus has increasingly been directed at the central role of calcium in intracellular signal transduction. Calcium is a key factor in maintaining normal cell membrane function, and calcium flux over the cell membrane plays a central role in mediating intracellular signal transduction, which regulates multiple cellular functions. Furthermore, the expression of cellular surface cadherins, which is necessary to maintain intercellular contact, depends on the presence of calcium. Particularly on colon cancer cells the expression of cadherins correlates with the rate of differentiation and the clinical outcome (19).

Reduction of calcium concentration in intercellular fluid lowers cell response to growth regulating factors and reduces the permeability of cell membranes. When the calcium concentration is reduced, the rates of proliferation and dedifferentiation increase.

Calcium contributes to regulating all cell division and cell differentiation phases, primarily through activation of various protein kinases (cAMP-dependent kinase, Ca-calmodulin-dependent protein kinases, protein kinase C) (20,21). Calcium suppresses ornithine-decarboxylase, a tumour-promoting enzyme (14) and reduces the number of K-ras mutations in colonic epithelium stimulated with the carcinogen 1,2 dimethylhydrazine (22). K-ras mutations are one of the early genomic changes in the carcinogenesis. K-ras mutations occur in approximately 85 per cent of adenocarcinomas and approximately 55 per cent of adenomas, but ras mutations exist even in up to 50 per cent of ACF.

Elevated calcium values produce increased differentiation of epithelial cells with concurrent growth suppression, but neoplastic colonic epithelial cells presumably lose their calcium response at one of the late stages of the epithelium-carcinoma sequence (16).

Stimulation with carcinogens at the preneoplastic stage produces luminal proliferation of the colon crypt proliferating cells, an increased proliferation ratio and an increased incidence of ACF, which is also seen in individuals with an elevated risk of colon cancer (HNPCC and FAP patients). At calcium administration, cells in the crypts can be converted to a normal proliferation ratio and normal geographical distribution of non-dividing cells in the luminal two thirds of the crypts and proliferating cells at the bottom of the crypts (23).

Montoya R. G. et al, "Chemoprevention of gastrointestinal cancer." CANCER AND METASTASIS REVIEWS (1997) 16/3-4 (405–419) discloses several compounds used for the prevention of colon cancer. There is no mentioning of vitamin $D_3$ and the reference to Ca relates to the theory concerning formation of insoluble calcium soaps.

WO 96 41645 discloses the use of $COX_2$ inhibitors for use in the treatment of inflammation.

Pence B. C. et al: Experimental chemoprevention of colon carcinogenesis by combined calcium and aspirin (Meeting Abstract), Proc. Annu Meet AM Assoc Cancer Res (1994). Vol. 35, pp A3719. ISSN: 0197-016X describes that tumour burden was lowest in groups fed Ca or ASA during promotion only. Supplementation during progression was less effective.

Sokoloski, John A. et al: Introduction of the differentation of HL-160 romyelocytic leukemia cells by nonsteroidal anti-inflammatory agents in combination with low levels of Vit $D_3$; Leuk. Res (1998), 22(2), 153–161, 1998. This article discloses that $D_3$ has an increasing effect on NSAID; however, only derivatives with receptor-binding properties have this effect and $D_3$ analogues without receptor-binding effect and with the Ca increasing effect do not have this increasing effect on the NSAID. The study was performed with leukemia cells.

Colorectal carcinogenesis and Vitamin $D_3$:

Vitamin $D_3$ ($D_3$) increases serum calcium by furthering the absorption of calcium and phosphate from the intestinal canal and mobilising calcium from bones. $D_3$ is present in food; it is formed by ultraviolet radiation of 7-dehydrocholesterol, a provitamin present in human skin and in fatty tissues in many animals. $D_3$ metabolises by successive hydroxylation, first in the liver, into 25-hydroxycholecalciferol, and then in the kidneys to 1,25 dihydroxycholecalciferol (1,25DHC) or 24,25DHC, which are the hormonally active metabolites of $D_3$ (1,25DHC>24, 25DHC).

In addition to its anti-oxidative effect, 1,25DHC resembles steroid hormones in its chemical structure and mechanism of action as 1,25DHC passes the cell membrane and binds to a specific cytoplasmatic receptor protein. This hormone-receptor complex is activated during translocation into the cell nucleus where it binds to DNA and initiates mRNA transcription and protein synthesis. In the nuclear membrane receptors for 1,25DHC are situated (high affinity nuclear vitamin D receptors, VDR), which contribute to regulating the calcium flux over cell membranes (17).

1,25DHC modulates signal transduction, inhibits proliferation and DNA synthesis, modulates c-myc, c-fos and c-jun oncogenic expression, induces differentiation and presumably apoptosis. VDRs have been identified both in normal colonic mucosa and in colorectal carcinomas (24). 1,25DHC increases intracellular calcium and stimulates various protein kinases, 1,25DHC stimulates transcription of the calbindin D gene in colonocytes, which is believed to increase transcellular calcium absorption.

A potent upregulation (300–400 per cent) of VDR takes place in neoplastic colonocytes; this can be interpreted as an adaptive response to tumour cell growth, by which the cell increases its differentiation potential. This response disappears at more advanced stages of the disease (>T3), where it is assumed that the vitamin D defence mechanism becomes inactivated (25).

In vitro, 1,25DHC inhibits the growth of human colon cancer cell lines (LoVo) including CEA-producing cell lines. In vivo (mice), 1,25DHC can suppress growth of solid, human xenografts (17,26). A few cohort studies of human populations have shown a significant reduction in the risk of developing colorectal cancer at intake of vitamin $D_3$ (or its active metabolite 1,25DHC), resulting in serum concentrations above 20 ng/ml (6,7).

RDA for vitamin $D_3$ is 10 $\mu$g/day increasing to 20 $\mu$g/day in elderly women without oestrogen substitution (6,7,27). The recommended dose of 1,25DHC is 0.01 $\mu$g/kg BW three times a week. In osteoporosis studies, 0,75 $\mu$g/day has been shown to induce hypercalcaemia.

New synthetic $D_3$ analogue preparations have 100–200 times the antiproliferative effect and effect on differentiation and only 0.5 times the hypercalcaemic effect of 1,25DHC.

Two NCI-CB sponsored studies of 1,25DHC 0.5 $\mu$g or D3 400 IU and calcium carbonate 1500 mg have been initiated in 1994.

It is known from studies of bone mineral turnover that vitamin D and calcium are mutually dependent factors, and this has proved to be the case also in the regulation of cell division and cell differentiation.

Colorectal carcinogenesis and cyclooxygenase inhibitors (acetylsalicylic acid (ASA) and other NSAIDs) and CRC:

The regulating effect of cyclooxygenase inhibitors (COX inhibitors) on the colonic epithelium has been investigated in connection with the treatment of chronic inflammatory intestinal diseases and FAP.

A cancer preventive effect of COX inhibitors has not been identified in detail at the level of molecular biology, but it is considered to be related to the impact of these drugs on arachidonic acid metabolism and prostaglandin synthesis via blocking of cyclooxygenase enzymes (COX).

Two isomeric forms have been identified: $COX_1$ and $COX_2$:

$COX_1$ is the constitutive form. In the upper gastrointestinal tract it affects the protection of mucosa by inducing bicarbonate secretion and mucin production primarily through prostaglandin E (PGE), which is the quantitatively dominant product of the $COX_1$ turnover of arachidonic acid. $COX_2$ is an inducible form. It is particularly induced by inflammatory stimuli, and it catalyses the formation of proinflammatory cytokines, including $PGE_2$ and $PGF_\alpha$, which strengthen the mutagenic effect of carcinogens by proliferation induction, suppression of the immune system and stimulation of angiogenesis. $PGE_2$ exerts its inhibitory effect via negative feedback T-cell proliferation and lymfokine production.

Arachidonic acid (AA, 5,8,11,14-eicosatetraenoic acid) originates from the cell turnover of phospholipids (PL) located in the cell membrane. AA is primarily liberated from PL by hydrolysis of the ester binding that binds AA to PL. In most cell types this occurs by direct activation of the enzyme phospholipase A2. The phospholipase A2 activity constitutes the common factor regulating the rate of AA liberation, and thus the rate of production for all eicosanoids (PG, prostacydins, thromboxanes and leukotrienes).

AA metabolises via the COX pathway to eicosanoids which stimulate cell division, as it is seen in inflammatory conditions, or via the lipoxygenase pathway to hydroperoxides (HPETE) and hydroxy compounds (HETE). The third pathway for arachidonic acid metabolism is via cytochrome P450 to HETE and EET (epoxyeicosatrienic acid). It has been shown that blocking of the lipoxygenase activity inhibits growth-factor-induced colonic tumour cell proliferation (28).

The COX inhibitor ASA (aspirin and others) and its metabolite salicylate block the formation of PG from AA by irreversible acetylation of COX (29), denying AA access to the active part of the enzyme. The COX activity can only be re-established by production of new COX molecules, and therefore cells without protein synthesis, such as platelets, are not capable of resuming COX activity. The main chemopreventive effect of ASA is deemed to be $COX_2$ inhibition (30), which results in metabolising of AA via a lipoxygenase pathway to 15-HETE (leukotriene with anti-inflammatory and antimitogenic effects).

Most other NSAIDs (piroxicam, sulindac and indomethacin) block COX in a reversible and dose-dependent manner, and ASA is therefore a more potent PG inhibitor. As will be apparent from the above, there are several mechanisms of action, and the PG cascade also depends on the calcium-regulated signal transduction system (21).

Several classic carcinogens are used as electron donors during the COX reaction, and they are activated by this reaction (high DNA affinity). Among them are polycyclic aromatic hydrocarbons, aflatoxins, halogenated pesticides, aromatic amines and phenol compounds. Thus, COX activates potential carcinogens into active DNA harmful metabolites.

In vitro studies show that most NSAIDs have an antiproliferative effect on human colon cancer cell lines (Ht-29, SW-80, DLD-1) (31).

In vitro studies also show that although the NSAID effect on the PG-synthesis is eliminated (for instance by the use of sulindac metabolites without COX inhibition), the growth of human colon cancer cell lines is nevertheless inhibited. This points to several mechanisms of action, including the ability significantly to induce apoptosis (28,32), and modulation of transmembrane calcium flux and intercellular junctions (33).

NSAID has been shown to inhibit several endonucleases; these are enzymes that cleave DNA molecules. Presumably they play a central part in the genomic instability which is one of the characteristics of colorectal multistep carcinogenesis (32). Other molecular biology mechanisms are discussed in detail in (35).

An interesting point is that, contrary to other NSAIDs, ASA has been shown to inhibit proliferation and lumen formation in cocultivated normal colon epithelial cells (carcinoma cells in compartment 2). This is taken as an expression of inhibition of the growth promoting signals of carcinoma cells. Other areas in which ASA differs from other NSAIDs are irreversible COX inhibition, lower plasma binding (approximately 50 per cent as compared to approximately 90 per cent).

Human colorectal neoplasms, both adenomas and adenocarcinomas, have been found to produce large amounts of PG, especially of the E type (31,36), and precisely $COX_2$ activity has been found to be accentuated 2 to 50-fold in 85 to 90 per cent of colorectal carcinomas (35). Particularly APC loss of heterozygocity (LOH) is believed to stimulate $COX_2$ expression at an early stage of neoplastic development in both epithelial and stroma cells. However, it may precisely be the stromal $COX_1$ activity that stimulates the expression of various angiogenetic factors (VEGF, bFGF and $TGF_{\beta 1}$).

Other proneoplastic effects of COX are the change of TGF-beta from an anti-proliferative growth factor to a pro-proliferative growth factor and reduced intercellular and cellular-stromal contact/communication, thus promoting angiogenesis and metastasis. These properties of COX suggest that inhibitions of both isoforms may have important effects against CRC (38).

In itself, one of the three domains of the COX molecule (COX domain, EGF-domain and membrane binding motif) resembles the epidermal growth factor (the ligand for the EGF receptor is also $TGF_\alpha$). For this reason a possible inactivation of the entire domain would be interesting in an attempt to achieve optimum prophylaxis.

Several major epidemiological studies of COX inhibitors in the form of cohort studies, case-control studies and prospective interventional studies have shown a significant preventive effect (reduction of relative risk of 40 to 50 per cent) particularly of ASA on CRC after long-term (2 to 10 years) therapy in the doses used to prevent ischaemic heart disease (11–13, 3942). In a cohort of patients with ulcerative colitis, a relative risk reduction of 0.38 (0.2 to 0.7) has been found following only 3 months of sulphasalazine therapy.

Animal trials have been able to demonstrate a significant protective effect (50 to 60 per cent) of for instance indomethacin and piroxicam in rats exposed to the carcinogen dimethylnitrosamine or azoxymethane (methylazoxymethanol) (43–46).

The most frequent undesirable effects connected with long-term administration of NSAIDs are gastroduodenal ulceration and bleeding because of low PG and thromboxane $A_2$ levels in the gastrointestinal tract. PG stimulates mucin production and bicarbonate secretion, and thromboxane $A_2$ indicates platelet aggregation. These complications are primarily related to inhibition of the constitutive $COX_1$ enzyme.

Undesirable effects and complications primarily relate to the use of NSAIDs as analgesic or anti-inflammatory agents in significantly higher doses, but they are potential sequels after long-term use also in lower doses.

A review of 16 cohort studies and case-control studies showed that the risk of developing severe NSAID-induced gastrointestinal undesirable effects amounts to 2 to 4 per cent a year at analgesic and anti-inflammatory daily doses (14). In low-dose aspirin prophylaxis of cardiovascular disease the relative risk-reduction in relation to stroke, acute myocardial infarction and/or cardiovascular death was found to be approx. 25% (47).

The Physicians' Health Study (325 mg of acetylsalicylic acid qod) found that, in addition to a significant reduction of the risk of acute myocardial infarct, there were significantly more cases of melaena and epistaxis than in the placebo group, but of neither cerebral haemorrhage nor unspecific gastrointestinal bleeding (including haematemesis) (39).

There exist numerous data on the pharmacokinetics and toxicity of COX inhibitors, especially regarding ASA. The FDA has found that for instance acetylsalicylic acid is a safe and efficient anti-inflammatory and analgesic agent and well suited for over-the-counter sales. No further toxicological studies are necessary to assess the usage of acetylsalicylic acid in chemoprevention (48–49).

The carcinogenesis in colorectal cancer involves a number of genetic changes and epigenetic factors such as increased expression of growth factors and suppression of growth inhibitors, which does not necessarily imply underlying mutations (but which for instance occurs at increased COX expression). Data from epidemiological studies and animal trials show that vitamin $D_3$ and calcium may be pharmacologically active when used as chemoprophylaxis of CRC. However, the effect is moderate. Some epidemiological studies in human populations indicate a reduction (40 to 50 per cent) of the relative cancer risk in populations using ASA continuously; there is not, however, consensus as to the dosage and duration of treatment. The risk-reduction in relation to CRC could be twice the risk-reduction of cardiovascular events.

BRIEF DESCRIPTION OF THE INVENTION

No prospective, randomised, double-blind studies exist. Studies of cancer chemoprophylaxis are extremely expensive, since they perforce have to include a very high number of individuals and run for years if the study end-points are to be invasive cancer and cancer-related mortality. For these reasons there is an increasing tendency towards relying on epidemiological studies of intermediary endpoints (eg, polyps, ACF, etc), animal trials of genetically engineered or carcinogenically stimulated animal populations and biological models for examining different biomarkers (mutations, growth factors, etc).

According to the present invention, the CRC preventive effect of the following combination of preparations manifests itself by a significant reduction of the incidence and overall morbidity and mortality of colorectal cancer. To achieve this effect, however, it is believed to be important to take the preparation consistently as prophylaxis over a long time (probably more than one year), exactly as for the prevention of ischaemic heart disease and osteoporosis.

By combining ASA with 1,25DHC (or an analogue preparation) or with calcium, an additive or synergistic effect is achieved, so that the amounts of the individual drugs are presumably reduced and the toxicity thereby reduced to a negligible level. In a preferred embodiment, ASA is combined with both 1,25DHC (or an analogue preparation) and calcium.

According to the present invention, a surprising effect may be obtained by a combination dosage comprising individual drugs which exert their effects on specific areas of the carcinogenesis: modification of signal transduction and expression of oncogenes, reduction of carcinogenic impact on the colonic epithelium and intracellular and intercellular signal transduction, COX inhibition and probably apoptosis.

In a further aspect of the invention, the incidence of undesirable gastrointestinal effects with COX inhibitors can be reduced or eliminated by prior eradication treatment of patients testing positive for *Helicobacter pylori*, who have been tested before initiation of chemoprophylaxis with a urease breath-test.

In a preferred embodiment, the individual subject to be treated is a mammal, preferably a human which due to underlying disease or a genetic defect is in risk of developing colorectal cancer such as: HNPCC patients, polyp patients, patients with a history of CRC. In addition, individuals over 50 years, who are first-degree relatives of patients with colorectal cancer (risk of developing CRC 2 to 4 times increased (12 to 25 per cent).

For first-degree relatives of individuals with CRC diagnosed before the age of 50 years or for individuals with two first-degree relatives with CRC, the risk increases 4 to 6 times (24 to 36 per cent) regardless of age.

For carriers of HNPCC mutations, the risk of CRC is 75 per cent at the age of 65 years and the risk of metachronous cancer is 45 per cent ten years following resection of the primary tumour.

For patients with chronic inflammatory intestinal diseases (ulcerative colitis and Crohn's disease), the risk increases 4 to 25 times (lifetime risk 12 to 75 per cent in patients not treated with surgery after more than ten years of illness) depending on the dissemination and duration of the disease.

Accordingly, in the use and method according to the present invention, the preferred embodiment is one wherein the human is selected from the group being in risk of development of colorectal cancer due to being a first-degree relative to a patient with colorectal cancer, and/or because he carries the gene(s) for hereditary non-polyposis colorectal cancer (HNPCC), and/or has familial adenomatous polyposis, colorectal adenomas and/or an inflammatory bowel disease such as ulcerative colitis or Crohns disease.

The preparations could be combined as follows:
15 500 mg of Calcium (calcium carbonate 1250 mg) and/or
0.5 µg of 1,25DHC (or a vitamin $D_3$ 400 IU or $D_3$ analogue, eg, 0.25 µg of calcitriol or 0.005 µg of calcitriol/kg BW) and
75 mg of ASA or an analogous reversible or irreversible $COX_2$ inhibitor The main requirements for a preparation designed for chemoprophylaxis include: low price, high compliance and ultra-low toxicity; it is assumed that by adding 1,25DHC and calcium, the amount of COX inhibitor (ASA) can be reduced, so that the ASA-related undesirable effects can be reduced to a negligible level without reducing its action. For acetylsalicylic acid, the undesirable effects following long-term use have made the FDA hesitate before approving acetylsalicylic acid as chemoprophylaxis of CRC.

Preparations with specific action in the colon, such as for instance 5-ASA, may turn out to be appropriate, possibly in combination with mucosa-protective agents.

ASA and other NSAIDs are approved for over-the-counter sales for analgesic and anti-inflammatory use. Similarly, combination preparations containing $D_3$ and calcium (for instance calcium carbonate 1250 mg=calcium 500 mg+$D_3$ 400 IU) are sold over-the-counter for osteoporosis prophylaxis.

At first, in vivo studies of the effect of the above have been carried out in the form of animal experiments with the Institute for Toxicology of the Danish Veterinary and Food Administration (DVFA). The results of the studies are shown in Table 1.

Apart from the chemopreventive effect on CRC chemoprevention from the use of a combination of a cyclooxygenase inhibitor, vitamin D3 or an analogue or metabolite thereof and calcium can also be expected on lung cancer carcinogenesis, urinary bladder cancer carcinogenesis and gynaecological cancer carcinogenesis.

In human and in animal studies, the first steps in the multistep carcinogenesis characterizing cancer development in lung mucosa, urinary bladder mucosa and mucosal tissues of the reproductive system (the adenoma-carcinoma sequence which results in the formation of adenocarcinomas) have many identical aspects to colorectal cancer with regard to pathology, involved genetic changes (mutations) and down-stream effects hereof irrespective in which of the above organs they arise.

Mutual events in molecular biology during carcinogenesis in the respiratory tract, gastrointestinal tract, urinary tract and reproductive system are seen in a range of different cellular mechanisms:

Genetic changes during early carcinogenesis: APC mutations and beta-catenin mutations (53, 54), DNA hypomethylation (55), p53 mutations (during promotion progression)

Down-stream effects on growth-promoting oncogenes and growth factors: myc and ras upregulation (56), EGF overexpression (57)

Down-stream effects on growth-inhibiting tumour suppressor genes and growth factors: reduced levels of expression of TGF-beta (58)

Down-stream effects on enzyme expression and metabolism: COX2 overexpression (59, 60, 61, 62), COX1 overexpression (63), increased PgE(2) synthesis (57, 63)

In animal studies on lung cancer, non-steroidal anti-inflammatory agents (NSAID) are shown to counteract the carcinogenesis initiated by the lung-tumour producing chemicals (64).

Accordingly, the scope of the present invention also encompasses methods of treatments similar to the methods of treatments disclosed with respect to colorectal cancer which methods are directed towards chemoprevention for other cancers, such as lung cancer carcinogenesis, urinary bladder carcinogenesis and gynaecological cancer carcinogenesis, and pharamceutical compositions similar to the pharmaceutical compositions disclosed for colorectal cancer for the use therefor. To investigate the chemopreventive effect of the combination of a cyclooxygenase inhibitor, 1,25 Dihydroxycholecalciferol and calcium, research protocols are developed to conduct animal experimental trials using appropriate rodent models of chemically induced carcinogenesis well known to the person of skill in the art. The experimental rodent models are attractive because a substantial overlap exists between man and mouse/rat in the genetic alterations thought to be responsible for tumourigenesis. An example of such a trial is a trial using the A/J mouse lung cancer model wherein the carcinogen stimulation is provided by a benzpyrene product delivered by a gastric tube which study runs for 30 weeks with various combinations of ASA, 1,25 DHC and calcium. The endpoints are precursors lesions such as atypical adenomatous hyperplasia of the lung.

DETAILED DESCRIPTION OF THE INVENTION

In one embodiment, the invention relates to a method for reducing the effective dosage of ASA in a chemoprofylactive treatment of colorectal cancer in a human by co-administration with a non toxic dosage of a vitamin $D_3$ including analogues and metabolites thereof and/or Ca in the form of a combination dosage. This is due to the fact it has surprisingly been shown that the addition of the vitamin $D_3$ and calcium may decrease the necessary dosage of acetylsalisylic acid in order to decrease the formation of abberant crypt foci in a model rat both with respect to size and numbers. Accordingly, the invention also relates to a method for the prevention of the initiation and/or progression of colorectal cancer in a human comprising administering to the human a combination dosage of a cyclooxygenase (COX) inhibitor, a vitamin $D_3$ including analogues and metabolites thereof and calcium.

By prevention and chemoprofylactive effect is meant prevention of colorectal cancer or the initiation and/or progression of colorectal cancer and/or the effect of reducing the formation of conditions being pre-malignant of colorectal cancer.

According to the present invention, it is believed that the administration of the combination dosage should be carried out regularly with an average daily dosage of the cyclooxygenase inhibitor corresponding to the inhibition of $COX_1$ and/or $COX_2$ provided by a dosage of ASA in the range of 50 mg and 500 mg, preferably in the range of 25 to 400 mg, more preferred in the range of 50 to 300 mg, still more preferred in the range of 75 to 150 mg, such as in the range of 75 to 100 mg.

The combination dosage may further comprise a vitamin $D_3$ including analogues and metabolites thereof corresponding to the antiproliferative and/or cell differentiation effect of the vitamin $D_3$ metabolite 1,25 dihydroxycholecalciferol in the range of 0.1 microgram to 2 micrograms.

Any calcium in the combination dosage may preferably be in the range of 200 mg to 3500 mg such as calcium in the range of from 250 mg to 3000 mg, such as in the range of from 300 mg to 2500 mg, preferably in the range of 400 to 2000 mg, more preferred in the range of from 500 to 1000 mg, such as 750 mg.

As mentioned above, the treatment or prevention should be continued for a long period in order to give the best effect; however, it is believed that a beneficial effect may be obtained after a treatment of at least 3 months. Accordingly the administration is preferably continued for at least 6 months, such as a least for 1 year, preferably for at least 2 years. However, persons in high risk may be treated according to the present invention for the rest of their lives.

In an important aspect, the administration of the combination dosage results in the prevention of the initiation or progression of colorectal cancer exceeding the effect of the administration of any of the individual ingredients in the same daily dosage and in the same period.

In another aspect, the method according to the invention is one wherein the combination dosage has a preventive effect which is at least additive compared with the effect of the individual effective ingredients. In one embodiment, the preventive effect is at least synergistic compared with the effect of the individual effective ingredients.

An additive effect according to the invention may be calculated as an effect of the sum of prevention by each of the substances ASA, the Vitamin $D_3$ and the Ca, respectively or by an effect of the sum of prevention by the selection of two of the substances ASA, the Vitamin $D_3$, and the Ca and the preventive effect by the remaining substance.

By synergistic effect according to the present invention is preferably meant an effect which is higher than the additive effect as disclosed above. A suitable reference for the calculation is disclosed in Example 1 disclosing a study of the formation of aberrant crypt foci in induced rat colon.

The COX inhibitor may be any one acting on one or more of the mechanisms selected from reversible or irreversible acetylation of $COX_1$ reversible or irreversible acetylation of $COX_2$, inhibition of angiogenesis, inhibition of arachidonic acid metabolism, blocking of AA metabolism, inhibition of the stimulation of proliferation stimulation from Epidermal Growth Factor, and stimulation of apoptosis. In a preferred embodiment, the COX inhibitor is primarily a $COX_2$ inhibitor. The preferred COX inhibitor is ASA. The preferred vitamin $D_3$ is 1,25 dihydroxycholecalciferol.

The ASA is preferably acting by one or more of the following mechanisms: inhibition of cell proliferation; inhibition of upregulation of proproliferative agents such as growth factors; modulation of signal transduction; and induction of apoptosis. Also inhibition of angiogenesis, and inhibition of arachidonic acid metabolism may be the target for the ASA. In a further aspect, the cyclooxygenase inhibitor acts by decreasing the formation of potential carcinogens into DNA harmful metabolites.

The vitamin $D_3$ including analogues and metabolites thereof are preferably acting by one or more of the following mechanisms: inhibition of cell proliferation; inhibition of DNA synthesis; modulation of signal transduction; induction of differentation; and induction of apoptosis.

In an important aspect of the invention, the vitamin $D_3$ is a synthetic analogue having an hypercalcaemic effect of 0.5 of the hypercalcaemic effect of 1,25 dihydroxycholecalciferol. A number of synthetic vitamin D analogues suitable according to the present invention are disclosed herein. In order to substitute one vitamin $D_3$ analogue according to the present invention, the relevant dosage may be correlated to the effect of 1,25 dihydroxycholecalciferol by reference to the antiproliferative effect which may be evaluated by methods well-known in the art, such as disclosed in references 17 and 26 herein.

According to the present invention, the active mechanism of the calcium is preferably an effect on the expression of cellular surface cadherins and/or intra- or extracellular signal transmission.

In an interesting embodiment, the invention relates to the finding that if the patient during or prior to the administration of the combination dosage receives treatment for *Helicobacter pylori*, any undesired effect of the dosage may be decreased.

One very important aspect of the the present invention is the finding that the method may reduce the risk of developing colorectal cancer in the individual human receiving the treatment by at least 10% or more compared to the effect obtained by any of the individual ingredients in the same dosage and during the same period of administration. The reduction may be at least 20% or more, and in certain circumstances e.g. for high risk patients even 30% or more, preferably about 50%. The period used for measurement may be at least 3 months, such as at least 6 months, most preferred at least 1 year, such as at least 2 years. The effect may be measured as disclosed in the example by the number of aberrant crypt foci in AOM induced rats receiving administration of the combination dosage.

One preferred combination dosage according to the invention is the combination dosage comprising ASA, 1,25 DHC and Ca because these ingredients are all well known drugs.

In a still further embodiment, the invention relates to the use of a cyclooxygenase (COX) inhibitor, a vitamin $D_3$ and/or calcium together with a pharmaceutically acceptable carrier for the preparation of a medicament for preventing the initiation and/or progression of colorectal cancer in a human. In a preferred embodiment, the medicament is in the form of a combination dosage comprising the cyclooxygenase (COX) inhibitor, the vitamin $D_3$ and/or the calcium.

The use may be in accordance with any of the methods described above and in a still further embodiment, the invention relates to any such pharmaceutical medicament. The pharmaceutical medicament may accordingly comprise a combination of a cyclooxygenase (COX) inhibitor, a vitamin $D_3$ including analogues and metabolites thereof and/or calcium. In a further aspect, the pharmaceutical medicament is such a medicament in any of the disclosed combination dosages which is to be administered according to any of the methods described herein.

Accordingly, a further aspect of the invention relates to the use of a cyclooxygenase (COX) inhibitor, a vitamin $D_3$ including analogues and metabolites thereof and calcium together with a pharmaceutically acceptable carrier for the preparation of a medicament for preventing the initiation and/or progression of colorectal cancer in a human.

In a still further aspect, the present invention relates to a pharmaceutical medicament comprising a combination of a cyclooxygenase (COX) inhibitor, a vitamin $D_3$ including analogues and metabolites thereof and calcium in a combination dosage together with a pharmaceutically acceptable carrier.

The pharmaceutical medicament according to the invention is preferably a medicament wherein the combination dosage comprises vitamin $D_3$ including analogues and metabolites thereof corresponding to the antiproliferative and/or cell differentiation effect of the vitamin $D_3$ metabolite 1,25 dihydroxycholecalciferol in the range of 0.1 μg to 2 μg such as in the range of 0.2 μg to 1.5 μg, preferably in the range of from 0.3 to 1 μg, more preferred in the range of from 0.4 μg to 0.75 μg, such as 0.5 μg.

In a further embodiment, the pharmaceutical medicament is one wherein the combination dosage comprises calcium in the range of 200 mg to 3000 mg, such as in the range of from 300 mg to 2500 mg, preferably in the range of 400 to 2000 mg, more preferred in the range of from 500 to 1000 mg, such as 750 mg.

In a preferred embodiment, the pharmaceutical medicament according to the invention is one wherein the combination dosage comprises ASA in the range of 50 mg to 500 mg, preferably in the range of 25 to 400 mg, more preferred in the range of 50 to 300 mg, still more preferred in the range of 75 to 150 mg, such as in the range of 75 to 100 mg. The most preferred medicament comprises 50 to 75 mg of ASA, 500–1000 mg of Ca, and 0.5 to 1 μg of 1,25 dihydroxycholecalciferol.

By a dosage according to the present invention is meant individual dosages for instance in one packet or a physical entity of one or more of the ingredients. The combination dosage may also comprise different COX inhibitors as well as different vitamin $D_3$ analogues and/or metabolites.

Accordingly, in a preferred embodiment, the pharmaceutical is one pharmaceutical comprising all three ingredients in order to secure the right individual dosage and patient compliance.

In a preferred embodiment the vitamin $D_3$ has a limited Ca inducing effect on the Ca level. Accordingly, the $D_3$ is preferably a synthetic analogue having a hypercalcaemic effect of the most 0.5 of the hypercalcaemic effect of 1,25 dihydroxycholecalciferol, calculated on a molar basis. This may be measured by methods known in the art. In the following relevant derivatives are disclosed.

In a still preferred embodiment, the vitamin $D_3$ analogues or derivatives are any one of the following disclosed in the references as mentioned.

WO 89/10351, which is hereby incorporated by reference, mentions the following vitamin D analogues:

A compound of the formula I

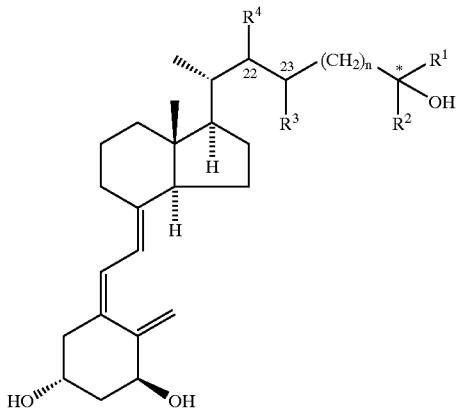

in which formula n is an integer from 1–7; and $R^1$ and $R^2$, which may be the same or different, represent hydrogen, or straight or branched, saturated or unsaturated $C_1$–$C_7$-alkyl; with the provisos that when n=1, $R^1$ and $R^2$ cannot simultaneously be hydrogen, nor can $R^1$ and $R^2$ simultaneously be an alkyl group independently chosen from methyl, ethyl and normal-propyl, and when n=2, $R^1$ and $R^2$ cannot simultaneously be methyl; or $C_3$–$C_8$-cycloalkyl, or, taken together with the carbon (starred in formula I) bearing the hydroxyl group, $R^1$ and $R^2$ can form a saturated or unsaturated $C_3$–$C_8$ carbocyclic ring; and $R^3$ and $R^4$ represent either both hydrogen, or when taken together constitute a bond, such double bond (either in the Z or E configuration) connecting carbons numbered 22 and 23; and derivatives of the compounds of formula I in which one or more hydroxy groups have been transformed into —O-acyl or —O-glycosyl or phosphate ester groups, such masked groups being hydrolysable in vivo, or derivatives of the compounds of formula I in which the hydroxyl group at the starred carbon atom is lacking, these compounds being converted to active compounds of formula I by enzymatic hydroxylation after administration.

In particular a diastereoisomer of a compound mentioned above, in pure form; or a mixture of diastereoisomers of a compound mentioned above.

Moreover, a compound according to the above mentioned specifications, selected from the group consisting of 1(S),3(R)-Dihydroxy-20(R)-(5-ethyl-5-hydroxy-1-heptyl)-9,10-secopregna-5(Z),7(E),10(19)-triene;

1(S),3(R)-Dihydroxy-20(R)-6-hydroxy-6-methyl-1-heptyl)-9,10-secopregna-5(Z),7(E),10(19)-triene;

1(S),3(R)-Dihydroxy-20(R)-(6-hydroxy-6-methylhept-1(E)-en-1-yl-9,10)-secopregna-5(Z),7(E),10(19)-triene;

1(S),3(R)-Dihydroxy-20(R)-(6-ethyl-6-hydroxy-1octyl)-9,10)-secopregna-5(Z),7(E), 1

1(S),3(R)-Dihydroxy-20(R)-(7-hydroxy-7-methyl-1-octyl)-9,10)-secopregna-5(Z),7(E), 10(19)-triene;

1(S),3(R)-Dihydroxy-20(R)-(6'-methyl-1'-heptyl)-9,10-secopregna-5(Z),7(E), 10(19)-triene;

WO 93/19044, which is hereby incorporated by reference, mentions the following vitamin D analogues:

A compound of the formula I

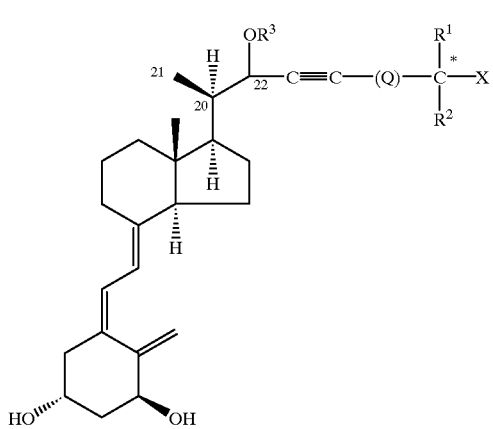

in which formula X is hydrogen or hydroxy; $R^1$ and $R^2$, which may be the same or different, represent hydrogen or a $C_1$–$C_6$ hydrocarbyl radical; or $R^1$ and $R^2$, taken together with the carbon atom (starred in formula I) bearing the group X, can form a $C_3$–$C_8$ carbocyclic ring; $R^3$ represents hydrogen or a $C_1$–$C_{10}$ hydrocarbyl radical or $YR^4$, in which Y represents the radicals —CO—, —CO—O—, —CO—S—, —CS—, —CS—O—, —CS—S—, S—SO—OR—SO$_2$—, and $R^4$ represnts hydrogen or a $C_1$–$C_{10}$ hydrocarbyl radical; Q is a single bond or a $C_1$–$C_8$ hydrocarbylene diradical; $R^1$, $R^2$, $R^3$, and /or Q may be optionally substituted with one or more deuterium or fluorine atoms.

In particular a diastereoisomer of a compound mentioned above, in pure form; or a mixture of diastereoisomers of a compound mentioned above.

Moreover, a compound according to the above mentioned specifications, selected from the group consisting of 1(S),3(R)-Dihydroxy-20(R)-(1,5-dihydroxy-5ethyl-2-heptyn-1-yl)-9,10-seco-pregna-5(Z),7(E), 10(19)-triene;

1(S),3(R)-Dihydroxy-20(R)-(5-ethyl-5-hydroxy-1-methoxy-2-heptyn-1-yl)-9,10-seco-pregna-5(Z)7(E), 10(19);

1(S),3(R)-Dihydroxy-20(R)-(1-ethoxy-5-ethyl-5hydroxy-2-heptyn-1-yl)-9, 10) -seco-pregna-5(Z),7(E), 10(19)triene;

1(S),3(R)-Dihydroxy-20(R)-(1-methoxy-4-hydroxy-4-ethyl-2-hexyn-1-yl)-9,10-seco-pregna -seco-pregna-5(Z),7(E), 10(19)-triene;

1(S),3(R)-Dihydroxy-20(R)-(1-ethoxy-4-hydroxy-4-ethyl-2-hexyn-1-yl)-9,10)-seco-pregna-5(Z),7(E), 10(19)-triene;

isomer A.

WO 94/14766, which is hereby incorporated by reference, mentions the following vitamin D analogues:

A compound of the formula I

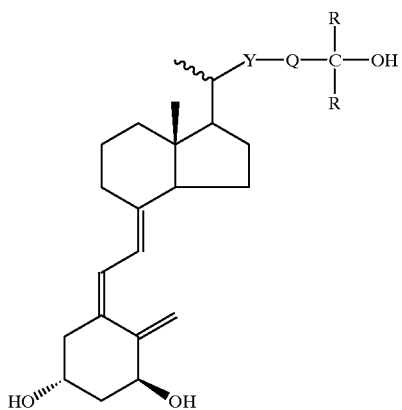

in which formula Y is sulfur, S(O), or S(O)$_2$; R represents $C_1$–$C_3$ alkyl; or R—C—R can form a $C_3$–$C_6$ carbocyclic ring; Q is a $C_1$–$C_8$ hydrocarbylene diradical; and prodrugs of I in which one or more of the hydroxy groups are masked as groups which can be reconverted to hydroxy groups in vivo.

A compound of the formula I shown above in which Y is sulfur and Q is $C_2$–$C_4$-alkylene.

Moreover a stereoisomer of a compound according to the above mentioned specifications, in pure form; or a mixture of such stereoisomers.

Furthermore, a stereoisomer of a compound according to the above mentioned specifications having a saturated side chain with the R-configuration at C-20.

Furthermore, a compound according to the formula I which is a) 1(S),3(R)-Dihydroxy-20(R)-(4-ethyl-4-hydroxy-1-hexylthio)-5S(Z),7(E),10(19)-triene, b) 1(S),3(R)-Dihydroxy-20(R)-[5-methyl-5-hydroxy-1-hexylthio]-9,10-seco-pregna-S(Z), 7(E),10(19)-triene, c) 1(S),3(R)-Dihydroxy-20(R)-[3-(1-methyl-1-hydroxyethyl)benzylthio]-9,10-seco-pregna-5Z),7(E), 10(19)triene, or d) 1(S),3(R)-Dihydroxy-20(R)-(3-methyl-3-hydroxy-1-butythio)-9,10-seco-pregna-S(Z), 7(E),10(19)-triene.

WO 93/0909, which is hereby incorporated by reference, mentions the following vitamin D analogues:

Compounds of general formulae (I) and (II)

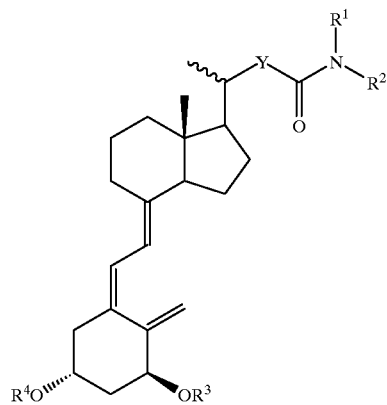

-continued (II)

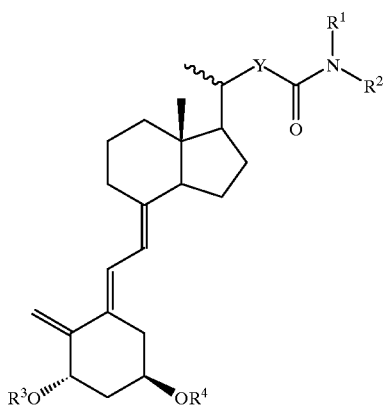

Compounds of general formula (I)

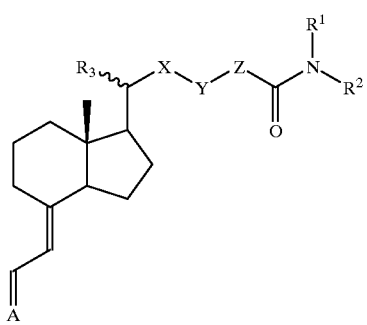

(I)

(wherein Y represents an alkylene or alkenylene group containing up to 4 carbon atoms; $R^1$ and $R^2$, which may be the same or different each represents a hydrogen atom or a lower alkyl or cycloalkyl group or together with the nitrogen atom to which they are attached form a heterocyclic group; and $R^3$ and $R^4$, which may be the same or different, each represents a hydrogen atom or an O-protecting group).

Moreover compounds according to the above mentioned compounds wherein Y represents a group of formula

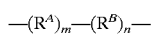

(wherein $R^A$ is —CH=CH—, $R^B$ is —CH$_2$—, m is 0, 1 or 2 and n is 0 or an integer such that 2m+n=1, 2, 3 or 4.

Furthermore, compounds according to the above mentioned compounds wherein Y is a $C_2$–$C_4$ alkylene group.

Compounds according to the above mentioned compounds wherein at least one of $R^1$ and $R^2$ is other than hydrogen.

Compounds according to the above mentioned compounds wherein $R^1$ and $R^2$ are selected from hydrogen atoms, methyl and cyclopropyl groups, or $R^1R^2N$— represents a piperidino group.

Compounds according to the above mentioned compounds wherein $R^3$ and $R^4$ represent etherifying silyl groups.

Compounds according to the above mentioned compounds wherein $R^3$ and $R^4$ are selected from hydrogen atoms and metabolically labile etherifying or esterifying groups.

Furthermore, the following compounds
1α,3β-dihydroxy-9,10seco-25-azacholest-5(Z),7,10(19)-trien-24-one;
1α,3β-dihydroxy-23,23-bishomo-24aza-9,10-secocholesta-5(Z),7,10(19)-trien-24-one;
1α,3β-dihydroxy-27-nor-9,10-secocholesta-5(Z),7,10(19),22,24-pentaene-26-carboxylic acid,26-dimethyl amide;
N,N-pentamethylene 1α,3β-dihydroxy-9,10-secocholanamide-5(Z),7,10(19)triene;
N-cyclopropyl-1α,3β-dihydroxy-9,10-secocholanamide-5(Z),7,10-(19)triene;
1α,3β-dihydroxy-9,10secocholanamide-5(Z),7,10(19) triene;
N,N-pentamethylene-1α,3β-dihydroxy-9,10-seco-20-epi-cholanamide-5(Z),7,10(19)-triene;
and corresponding 5(E)-isomers thereof.

WO 94/26707, which is hereby incorporated by reference, mentions the following vitamin D analogues:

where $R^1$ and $R^2$, which may be the same or different, each represents a hydrogen atom or an aliphatic, cycloaliphatic, araliphatic or aryl group or together with the nitrogen atom to which they are attached form a heterocyclic group; $R^3$ represents a methyl group having α- or β-configuration; X represents a valence bond or a $C_{1-2}$ alkylene group; Y represents —O—, —S—, —CH— or —NR— where R is a hydrogen atom or an organic group; Z represents a valence bond or a $C_{1-3}$ alkylene group; and A=represents a cydohexylidene moiety characteristic of the A-ring of a 1α-hydroxylated vitamin D or analogue thereof, with the proviso that when —X—Y—Z— together represent an alkylene group containing up to 4 carbon atoms, A=does not carry an exocyclic methylene group at the 10-position.

Compounds of the general formula (I) as shown above wherein A=represents one of the groups (A-2)

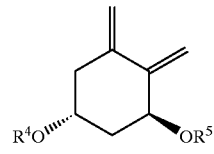

(A-3)

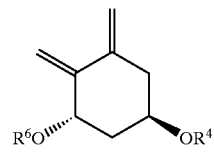

(A-4)

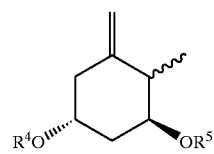

(A-5)

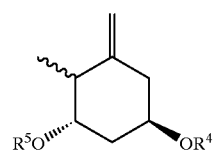

-continued

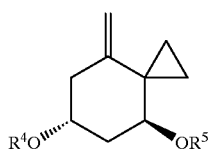
(A-6)

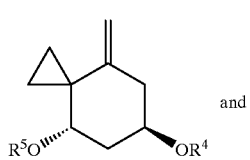
and
(A-7)

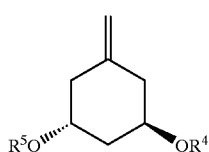
(A-8)

(where $R^4$ and $R^5$, which may be the same or different, each represents a hydrogen atom or an O-protecting group).

Moreover compounds of the general formula (I) and the specification mentioned above wherein $R^4$ and $R^5$ represent etherifying silyl groups.

Moreover compounds of the general formula (I) and the specification mentioned above wherein $R^4$ and $R^5$ are selected from hydrogen atoms and metabolically labile etherifying or esterifing groups.

Furthermore compounds of the general formula (I) according to the above specification wherein A=represents one of the groups

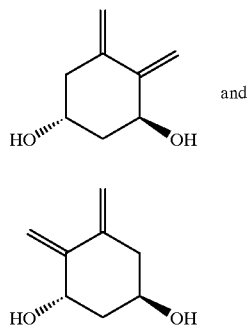
(A-2a)

and (A-3a)

Compounds of the above general formula (I) wherein $R^1$ and $R^2$ are selected from hydrogen atoms, $C_{1-6}$ alkyl groups, $C_{3-8}$ cycloalkyl groups, $C_{8-12}$ aryl $C_{1-4}$ alkyl and optionally substituted $C_{6-12}$ carbocyclic aryl groups.

Compounds of the above-specified general formula (I) wherein $R^1$ and $R^2$ are selected from hydrogen atoms, $C_{1-8}$ alkyl groups and $C_{3-8}$ cycloalkyl groups.

Compounds of the above-specified general formula (I) wherein $R^1$ and $R^2$ are selected from hydrogen atoms, methyl, ethyl, and cyclopropyl groups.

Furthermore, the following compounds
1α,3β-dihydroxy-20-epi-22-oxa-9,10-secochola-5(Z),7,10(19)-trienic acid, piperidine amide;
1α,3β-dihydroxy-20-epi-23-homo-22-oxa-9,10-secochola-5(Z),7,10(19-trienic acid, dimeth cyclopropylamine and piperidine amides;
1α,3β-dihydroxy-20-epi-22-oxa-9,10-secochola-5(Z),7,10(19)-trienic acid, morpholine amide;
1α,3β-dihydroxy-20epi-23-bis-homo-22-oxa-9,10-secochola-5(Z),7,10(19)-trienic acid, piperidine amide;
1α,3β-dihydroxy-20-epi-23-homo-23oxa-9,10-secochola5(Z),7,10(19)-trienic acid, piperi amide;
1α,3β-dihydroxy-23-homo-23-oxa-9,10-secochola-5(Z),7,10(19)-trienic acid, diethylamine, cyclopropylamine and piperidine amides and 20-epi analogues thereof;
1α,3β-dihydroxy-23-homo-23-oxa-9,10-secochola-5(Z),7-dienic acid, diethylamine, cyclopropylamine and piperidine amides and 29-epi analogues thereof:
1α,3β-dihydroxy-23-homo-23-oxa-10-spirocyclopropyl-9,10-secochola-5(Z),7-dienic acid, diethylamine, cyclopropylamine and piperidine amides and 20-epi analogues thereof;
1α,3β-dihydroxy-9,10-secochola-5(Z),7-dienic acid, piperidine amide;
1α,3β-dihydroxy-10-spirocyclopropyl-9,10-secochola-5(Z),7-dienic acid, piperidine amide;
1α,3β-dihydroxy-23-homo-9,10-secochola-5(Z),7-dienic acid, piperidine amide;
1α,3β-dihydroxy-23-homo-10-spirocyclopropyl-9,10-secochola-5(Z),7-dienic acid, piperidine amide:
1α,3β-dihydroxy-23homo-19-nor-9,10-secochola-5,7-dienic acid, piperidine amide;
1α,3β-dihydroxy-20epi-23-homo-9,10-secochola-5(Z),7-dienic acid, piperidine amide;
1α,3β-dihydroxy-20epi-23-homo-9,10-seco-23-thiachola-5(Z),7,10(19)trienic acid, piper amide;
23-aza-1α,3β-dihydroxy-20-epi-23-bis-homo-9,10-secochola-5(Z),7,10(19)-trienic acid, piperidine amide;
23-aza-1α,3β-dihydroxy-20-epi-23-homo-9,10-secochola-5(Z),7,10(19)trenic acid, piper amide;
1α,3β-dihydroxy-20-epi-19-nor-9,10-secochola-5,7-dienic acid, piperidine amide:
1α,3β-dihydroxy-23homo-19-nor-23-oxa-9,10-secochola-5,7-dienic acid, piperidine amide;
23-aza-1α,3β-dihydroxy-9,10-secochola-5(Z),7,10(19)-trienic acid, piperidine amide;
22-aza-1α,3β-dihydroxy-20-epi-23-homo-9,10-secochola-5(Z),7,10(19)-trienic acid, pipe amide;
23-aza-1α,3β-dihydroxy-9,10-secochola-5(Z),7,10(19)-trienic acid, diethyl amide and the 20-epi analogue thereof;
1α,3β-dihydroxy-9,10-secochola-5(Z),7,10(19)-trienic acid, N-methyl-N-phenyl amide and the 20-epi analogue thereof; and
1α,3β-dihydroxy-9,10secochola-5(Z),7-dienic acid, N-methyl-N-phenyl amide and the 20-epi analogue thereof.

WO 95/03273, which is hereby incorporated by reference, mentions the following vitamin D analogues:
Compounds of general formula (I):

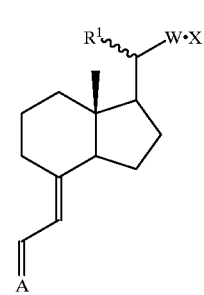
(I)

where $R^1$ represents a methyl group having α- or β-configuration; W represents a valence bond or a $C_{1-5}$ alkylene group; X represents azide or an optionally substituted triazole group; and A=represents a cyclohexylidene moiety characteristic of the A-ring of a 1α-hydroxylated vitamin D or analogue thereof.

Moreover compounds of the general formula (I) as shown above having the general formula (II)

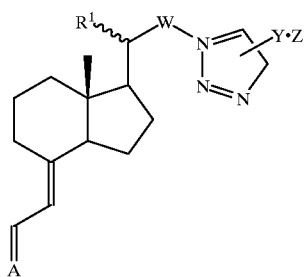

(II)

wherein $R^1$, W and A are as defined in claim 1; Y represents a valence bond or a lower alkylene group attached to the 4- or 5-position of the triazole ring; and Z represents either (i) a group —CO—$NR^2R^3$ in which $R^2$ and $R^3$ may be the same or different and are selected from hydrogen atoms, aliphatic, cycloaliphatic, araliphatic and aryl groups, or $R^2$ and $R^3$ together with the nitrogen atom to which they are attached form a heterocyclic group; or (ii) a group —$(R^4)(R^5)$·OH in which $R^4$ and $R^5$ may be the same or different and are selected from hydrogen atoms, aliphatic, cycloaliphatic, araliphatic and aryl groups, or $R^2$ and $R^3$ together with the cart>on atom to which they are attached form a $C_{3-8}$ carbocyclic ring.

Furthermore the compounds:
20α-(3-azidopropyl)-1α,3β-dihydroxy-9,10-secopregna-5(Z), 7,10(19)-triene;
20α-azido-1α,3β-dihydroxy-9,10-secopregna-5(Z),7,10(19)-triene;
1α,3β-dihydroxy-20α-[4-(2-hydroxyprop-2-yl)-1,2,3-triazol-1-yl]-9,10-secopregn-5(Z),7,10(19)-triene;
1α,3β-dihydroxy-20α-[4-(3-hydroxypent-3-yl)-1,2,3-triazol-1-yl]-9,10-secopregn-5(Z),7,10(19)-triene;
1α,3β-dihydroxy-20α-[4-(2-hydroxyprop-2-yl)-1,2,3-triazol-1-ylmethyl]-9,10-secopregna-5(Z),7,10(19)triene;
1α,3β-dihydroxy-20β-[4-(3-hydroxypent-3-yl)-1,2,3-triazol-1-ylmethyl]-9,10-secopregna-5(Z),7,10(19)-triene;
1α,3β-dihydroxy-20α-[4-(3-hydroxypent-3-yl)-1,2,3-triazol-1-ylmethyl]-9,10-secopregna-5(Z),7,10(19)-triene;
1α,3β-dihydroxy-20α-[4-(N,N-pentamethylenecarbamoyl)-1,2,3-triazol-1-ylmethyl]-9,10-secopregna-5(Z),7,10(19)-triene;
1α,3β-dihydroxy-20α-[4-(N,N-diethylcarbamoyl-1,2,3-triazol-1-ylmethyl]-9,10-secopregna-5(Z),7,10(19)-triene;
1α,3β-dihydroxy-20α-[4-(N-cyclopropylcarbamoyl)-1,2,3-triazol-1-ylmethyl]-9,10-secopregna-5(Z),7,10(19)-triene:
1α,3β-dihydroxy-20α-[4-(N,N-3-oxapentamethylencarbamoyl)-1,2,3-triazol-1-ylmethyl]-9,10secopregna-5(Z),7,10(19)-triene;
1α,3β-dihydroxy-20α-[4-(N,N-diisopropylcarbamoyl)-1,2,3-triazol-1-ylmethyl]-9,10-secopregna-5(Z),7,10(19)-triene;
1α,3β-dihydroxy-20α-[4-(N,N-pentamethylencarbamoyl)-1,2,3-triazol-1-ylmethyl]-9,10-secopregna-5(Z),7,10(19)-triene;
1α,3β-dihydroxy-20β-[4-(N,N-diethylearbamoyl)-1,2,3-triazol-1-ylmethyl]-9,10-secopregna-5(Z),7,10(19)-triene;
1α,3β-dihydroxy-20β-[4-(N-cyclopropylcarbamoyl)-1,2,3-triazol-1-ylmethyl]-9,10secopregna-5(Z),7,10(19)-triene;
1α,3α-hydroxy-20β-[4-(N,N-3-oxapentamethylenecarbamoyl)-1,2,3-triazol-1-ylmethyl]-9,10secopregna-5(Z),7,10(19)triene;
1α,3β-dihydroxy-20β-[4-(N, N-diisopropylcarbamoyl)-1,2,3-triazol-1-ylmethyl]-9,10-secopregna-5(Z),7,10(19)-triene;
1α,3β-dihydroxy-20α-{2-[4-(N,N-pentamethylenecarbamoyl)-1,2,3-triazol-1-yl]ethyl}-5(Z),7,10(19)triene;
1α,3β-dihydroxy-20α-{2-[4-(N,N-diethylcarbamoyl)-1,2,3-triazol-1-yl]ethyl}-9,10-secopregna-5(Z),7,10(19)-triene;
1α,3β-dihydroxy-20α-{-2-[4-(N-cyclopropylcarbamoyl)-1,2,3-triazol-1-yl]ethyl}-9,10-secopregna-5(Z),7,10(19)-triene;
1α,3β-dihydroxy-20α-{2-[4-(N,N-3-oxapentamethylenecarbamoyl)-1,2,3-triazol-1-yl]ethyl}-9,10-secopregna-5(Z),7,10(19)-triene;
1α,3β-dihydroxy-20α-{2-[4-(N,N-diisopropylcarbamoyl)-1,2,3-triazol-1-yl]ethyl}-9,10-secopregna-5(Z),7,10(19)-triene;
1α,3β-dihydroxy-20α-[4-(1-hydroxycyclohex-1-yl)-1,2,3-triazol-1-ylmethyl)]-9,10-secopregna-5(Z),7,10(19) triene;
1α,3β-dihydroxy-20α-{2-[4-(3-hydroxypent-3yl)-1,2,3-triazol-1-yl)ethyl}-9,10-secopregna-5(Z),7,10(19)-triene;
1α,3β-dihydroxy-20β{2-[4-(3-hydroxypent-3yl)-1,2,3-triazol-1-yl]ethyl}-9,10-secopregna-5(Z),7,10(19) triene;
1α,3β-dihydroxy-20β-{3-[4-(3-hydroxypent-3-yl)-1,2,3-triazol-1-yl]propyl}-9,10-secopregna-5(Z),7,10(19)-triene;
1α,3β-dihydroxy-20α-{3-[4-(3-methyl-3-hydroxybutyl)-1,2,3-triazol-1-yl)propyl}9,10-secopregna-5(Z),7,10(19)triene;
1α,3β-dihydroxy-20α-{3-[4-(2-methyl-2-hydroxypentyl)-1,2,3-triazol-1-yl)propyl}-9,10-secopregna-5(Z),7,10(19)-triene;
1α,3β-dihydroxy-20α-{3-[4-(4-ethyl-4-hydroxyhexyl]-1,2,3-triazol-1-yl]propyl }9,10-secopregna-5(Z),7,10 (19)-triene;
1α,3β-dihydroxy-20α-{3-[4-(2-hydroxybut-2-yl)-1,2,3-triazol-1-yl]propyl}-9,10-secopregna-5(Z),7,10(19) triene;
1α,3α-dihydroxy-20α-{3-[4-(4-methyl-2-hydroxypent-2-yl)-1,2,3-triazol-1-yl]propyl }9,10-secopregna-5(Z),7,10(19)-triene;
1α,3β-dihydroxy-20α-{3-[4-(2,4-dimethyl-3-hydroxypent-3-yl)-1,2,3-triazol-1-yl]propyl}9,10-secopregna-5(Z),7,10(19)-triene;
1α,3β-dihydroxy-20α-[4-(2ethyl-2-hydroxybutyl)-1,2,3-triazol-1-yl]-9,10-secopregna-5(Z),7,10(19)-triene;

1α,3β-dihydroxy-20α-[5-(2-ethyl-2-hydroxybutyl)-1,2,3-triazol-1-ylmethyl]-9,10-secopregna-5(Z),7,10(19)triene;
1α,3β-dihydroxy-20α-[4-(3-hydroxypent-3-yl)-1,2,3-triazol-1-ylmethyl]-9,10-secopregna-5(E),7-diene;
1α,3β-dihydroxy-20α-[4-(3-hydroxypent-3-yl)-1,2,3-triazol-1-ylmethyl)-9,10-secopregna-5(Z),7-diene;
1α,3β-dihydroxy-20α-[4-(3-hydroxypent-3-yl)-1,2,3-triazol-1-ylmethyl]-10-spirocyclopropyl-9,10-secopregna-5(E),7-diene;
1α,3β-dihydroxy-20α-[4-(3-hydroxypent-3-yl)-1,2,3-triazol-1-ylmethyl]-10-spirocyclopropyl-9,10-secopregna-5(Z),7-diene;
1α,3β-dihydroxy-20α-[4-(3-hydroxypent-3-yl)-1,2,3-triazol-1-ylmethyl]-19-nor-5,7-diene;
1α,3β-dihydroxy-20α-[4-(3-methyl-3-hydroxybutyl)-1,2,3-triazol-1-ylmethyl]-9,10secopregna-5(Z),7,10(19)triene;
1α,3β-dihydroxy-20α-[4-(2-methyl-2-hydroxypentyl)-1,2,3-triazol-1-ylmethyl]-9,10secopregna-5(Z),7,10(19)triene;
1α,3β-dihydroxy-20α-[4-(4-ethyl-4-hydroxyhexyl)-1,2,3-triazol-1-ylmethyl]-9,10-secopregna-5(Z),7,10(19)triene;
1α,3β-dihydroxy-20α-[4-(2-hydroxybut-2-yl)-1,2,3-triazol-1-ylmethyl]-9,10-secopregna-5(Z),7,10(19)triene;
1α,3β-dihydroxy-20α-[4-(4-methyl-2-hydroxypent-2-yl)-1,2,3-triazol-1-ylmethyl]-9,10-secopregna-5(Z),7,10(19)triene;
1α,3β-dihydroxy-20α-[4-(2,4-dimethyl-3-hydroxypent-3-yl)-1,2,3-triazol-1-ylmethyl]-9,10-secopregna-5(Z),7,10(19)-triene; and
1α,3β-dihydroxy-20α-[4-(2-hydroxypheneth-2-yl)-1,2,3-triazol-1-ylmethyl]-9,10-secopregna-5(Z),7, 19(19)triene.

WO 95/02577, which is hereby incorporated by reference, mentions the following vitamin D analogues, A compound of the formula I

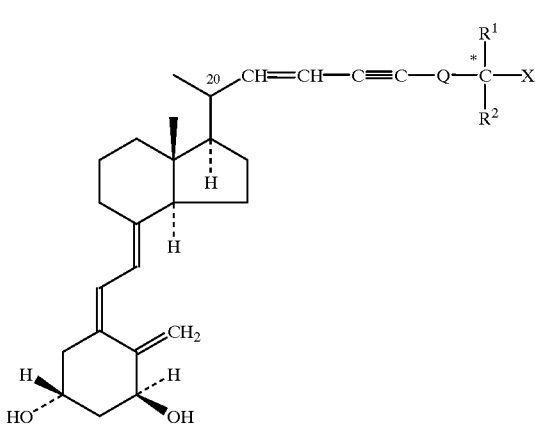

in which formula X is hydrogen or hydroxy, $R^1$ and $R^2$, which may be the same or different, represent hydrogen or $C_1$–$C_4$ hydrocarbyl; or $R^1$ and $R^2$, taken together with the carbon atom bearing the group X, can form a $C_3$–$C_8$ carbocyclic ring; Q is a single bond or a $C_1$–$C_4$ hydrocarbylene diradical, the expression hydrocarbyl radical (hydrocarbylene diradical) indicating the residue after removal of 1 (2) hydrogen atom(s) from a straight, branched or cyclic saturated or unsaturated hydrocarbon; $R^1$, $R^2$ and/or Q may be optionally substituted with one or more fluorine atoms; and prodrugs of I in which one or more of the hydroxy groups are masked as groups which can be reconverted to hydroxy groups in vivo.

European patent application No. 0 205 025 A1, which is hereby incorporated by reference, mentions the following vitamin D analogues:

A compound of the formula (I)

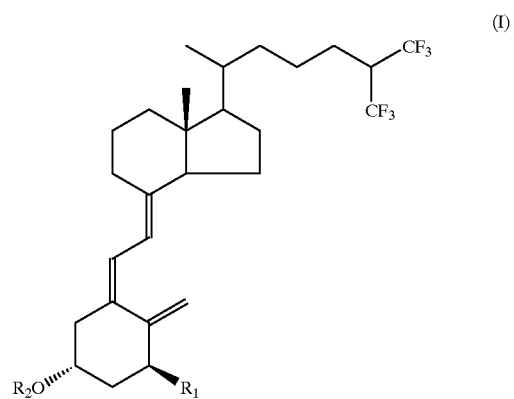

wherein $R_1$ is a hydrogen atom, a hydroxyl group or a protected hydroxyl group and $R_2$ is a hydrogen atom or a protecting group, such as 26,26,26,27,27,27-Hexafluoro-1α-hydroxyvitamin $D_3$.
26,26,26,27,27,27-Hexafluorovitamin $D_3$.

In addition to the ASA, the COX inhibitors according to the invention include other NSAIDS known in the art.

EXAMPLE 1

The influence of 1α,25 (OH)$_2$-vitamin $D_3$, calcium and acetylsalicylic acid on AOM-induced aberrant crypt foci and colorectal tumours in rat colon Materials and Methods Animals 128 male F344/Mol-rats, SPF (F344/Ntac@Mol) three to four weeks old were purchased from M & B (LI. Skensved, Denmark).

Diets

All groups of rats were offered a powdered purified diet. The amounts of 1α,25(OH)$_2$D$_3$, calcium and acetylsalicylic acid in the diet for each group are presented in Table 1.

Chemical

Azoxymethane (AOM) was obtained from Sigma Chemical (St. Louis, Mo.). 1α,25(OH)$_2$D$_3$ was provided by Leo Pharmaceutical Products, Ballerup, Denmark. Acethylsalicylic acid (ASA) was obtained from Nycomed Danmark A/S.

Housing

The animals were kept in disposable plastic cages with an inserted steel grid floor, two animals per cage, in flexible film isolaters (Isotec 12134, Olac, Oxford, UK) during the dosing period, and one week after the termination of the dosing with AOM. For the remaining period of the study, the animals were kept in stainless steel wire cages with two animals per cage. During the study, the temperature was maintained at 21±1° C., a relative humidity at 55±5%, air was changed 10 times/hr, and fluorescent light was on from 2100 to 0900.

Experimental Design

The animals were randomly assigned to eight experimental groups of 16 animals and fed their respective diets for 19 days (Table 1). Then all groups were dosed AOM, 15 mg/kg body weight subcutaneously twice one week apart The animals were maintained on their respective diets for a 16-week observation period. Body weight, food and water consumption were measured weekly. At the termination of the study, ten animals from each of the groups 1, 6, 7, and 8 were placed separately in metabolism cages for 24 hours. After rinsing with 10 ml of water the urine was collected for determination of volume, pH, calcium and creatinine. Eighteen weeks after the first AOM injection, the animals were sacrificed and serum was collected for future analysis of acetylsalicylic acid. The abdomen and thoracic cavity of all animals were examined to reveal macroscopic changes. The weight of kidneys and adrenals were recorded. These organs, the stomach, small intestine, and thyroid gland with parathyroids were preserved in 4% buffered formaldehyde, pending future requirement for histopathological examination. The large intestine was cut longitudinally, rinsed in 0.9% NaCl, and divided into two pieces of equal length, pinned on a cork slab, and fixed in cold 4% neutral buffered formaldehyde according to (1).

TABLE 1

Scheme of treatment

| Group | Animal no. | ASA ppm | 1α, 25(OH)$_2$D$_3$ μg/kg* | Ca Ppm |
|---|---|---|---|---|
| 1 | 1–16 | 0 | 0 | 5000 |
| 2 | 17–32 | 0 | 0 | 2500 |
| 3 | 33–48 | 0 | 0 | 7500 |
| 4 | 49–64 | 0 | 0.02 | 7500 |
| 5 | 65–80 | 300 | 0 | 7500 |
| 6 | 81–96 | 300 | 0.02 | 7500 |
| 7 | 97–112 | 300 | 0.02 | 5000 |
| 8 | 113–128 | 300 | 0.02 | 2500 |

*The content of vitamin D$_2$ in SYN 8 is unchanged 1000 IU/kg.

Urine Analysis

Analysis for creatinine and calcium was performed using a Combas Mira S analyser using the relevant kit for each parameter (Roche Diagnostic Systems).

Assessment of ACF

The ACF were visualised by Giemsa staining, recorded using a stereomicroscope at ×40 magnification, and grouped into small (1–3 crypts), medium (4–6 crypts), large (7–9 crypts), extra-large (>10 crypts), and ACF>7 (>7 crypts). The ACF were distinguished from normal according to (1).

Assessment of Tumours

Colonic tissue deviations suspected to be tumours at gross examination or under stereomicroscope were embedded in paraffin, sectioned at 4–6 μm, and stained with hematoxylin and eosin for histopathological examination.

Statistical Analysis

All data are presented as mean ±SE. One way analysis of variance with repeated measures on one factor was used to analyse body weight and food and water consumption. The analyses were followed by a Least Significant Difference test if significant. Data on organ weights, urine chemistry, and ACF were analysed by a one-way analysis of variance followed by a Least Squares Means. The homogeneity of variance among groups was evaluated by judgement of standard residual plots (General Linear Model procedure). Data on tumour bearing animals were analysed by Fishers exact test. A p<0.05 was considered significant. All statistical analyses were carried out using SAS release 6.12.

Results and Discussion

Urine Chemistry

The urinary volume, pH, concentration of calcium and creatinine of group 1, 6, 7, and 8 were examined (see Table 2). The concentration of calcium was statistically significantly decreased in groups 6 and 8. A non-significant decrease was observed in group 7 as well. The effect is likely to be caused by a 1α,25(OH)$_2$D$_3$ induced renal retention of calcium. The pH of group 7 was statistically significantly higher than the control value. As no significant changes were observed in groups 6 and 8, this is probably fortuitous. The results further demonstrate that no side effect of the combination treatment according to the invention is observed.

TABLE 2

Urine chemistry[a]

| Group[b] | N | volume ml | pH | calcium mmol/l | creatinine μmol/l |
|---|---|---|---|---|---|
| 1 | 10 | 11.3 ± 1 | 7.2 ± 1.1 | 6.57 ± 1.9 | 7062 ± 560 |
| 6 | 10 | 12.1 ± 2 | 6.9 ± 1.1 | 4.49 ± 1.6* | 7412 ± 858 |
| 7 | 10 | 11.8 ± 1 | 8.6 ± | 5.80 ± 2.0 | 7164 ± 429 |
| 8 | 10 | 12.0 ± 2 | 7.8 ± 1.1 | 2.8 ± 1.7* | 6370 ± 512 |

[a]Mean ± SD.
[b]Group 1, control diet (5000 ppm Ca); group 6, 0.02 μg 1α, 25(OH)$_2$D$_3$, 300 ppm acetyl-salicylic acid, and 7500 ppm Ca in the diet; group 7, 0.02 μg 1α, 25(OH)$_2$D$_3$, 300 ppm acetylsalicylic acid, and 5000 ppm Ca in the diet; group 8, 0.02 μg 1α, 25(OH)$_2$D$_3$, 300 ppm acetylsalicylic acid, and 2500 ppm Ca in the diet.
*denotes statistical significance to control group when a Least Square Means test was performed (p < 0.05).

Organ Weight

The relative organ weight was calculated per 100 g of body weight. The terminal body weight, the absolute weight of kidneys and adrenals, and the relative weight of adrenals were not affected by treatment. The relative kidney weight of groups 5 and 8 was increased when compared to the control group. The changes are minor and not believed to be related to treatment.

ACF and Tumours

ACF as intermediary bio-markers and not tumours/cancers were end-points for this study. Nevertheless a number of animals developed tumours during the trial. According to the adenoma-carcinoma sequence, tumours represent late-stage carcinogenesis and are therefore included in the results. Large ACF, x-large ACF and tumours represent lesions with significant correlation to subsequent invasive cancer and cancer related death. The group of animals with lesions containing more than seven crypts (ACF>7) is considered as high-risk animals with regard to cancer development.

The total number and distribution of ACF and tumours are presented in Table 3 and appendix 3.

Animals fed on a low calcium diet of 2500 ppm (mimicking an older, Western-world, human population) were most susceptible to ACF development. Increasing calcium levels in the diet significantly reduced the number of ACF. In animals fed 7500 ppm calcium and 1,25(OH)$_2$-D$_3$ a statistically significant decrease in the total number of ACF was observed when compared to groups 1 and 2 (35.1 vs. 61.7, and 35.1 vs. 88.3, respectively). In animals fed 7500 ppm calcium, 1,25 (OH)$_2$D$_3$ and ASA, a non-significant reduction in total ACF was observed when compared to group 1 (44.6 vs. 61.7).

TABLE 3

Mean number of aberrant crypt foci (ACF) or tumours in AOM-induced rats fed diets containing 1α,25(OH)$_2$D$_3$, acetylsalicylic acid, and various doses of Calcium[a–b]

| Group[c] | N | Total | Small | Medium | Large | Extra Large | Tumours | ACF > 7 crypts |
|---|---|---|---|---|---|---|---|---|
| 1 | 15 | 61.7 ± 8.4 | 39.8 ± 5.0 | 18.9 ± 3.4 | 2.3 ± 0.7 | 0.7 ± 0.3 | 0.2 ± 0.1 | 3.2 ± 0.8 |
| 2 | 16 | 88.3 ± 9.4 | 55.1 ± 6.3 | 27.6 ± 3.8 | 4.5 ± 0.9 | 1.1 ± 0.4 | 0.6 ± 0.2 | 6.1 ± 1.3 |
| 3 | 16 | 46.8 ± 8.7 | 35.4 ± 6.5 | 9.9 ± 2.3 | 1.0 ± 0.3 | 0.4 ± 0.2 | 0.9 ± 0.3 | 2.4 ± 0.6 |
| 4 | 16 | 35.1 ± 5.0 | 26.1 ± 3.5 | 7.5 ± 1.5 | 1.1 ± 0.3 | 0.4 ± 0.1 | 1.1 ± 0.3 | 2.6 ± 0.5 |
| 5 | 16 | 45.4 ± 5.7 | 33.0 ± 5.1 | 10.9 ± 1.7 | 1.2 ± 0.4 | 0.3 ± 0.1 | 0.5 ± 0.2 | 1.9 ± 0.6 |
| 6 | 16 | 44.6 ± 6.7 | 32.9 ± 5.0 | 10.4 ± 2.1 | 0.6 ± 0.3 | 0.6 ± 0.3 | 0.5 ± 0.2 | 1.8 ± 0.6 |
| 7 | 16 | 73.6 ± 8.8 | 52.2 ± 6.0 | 19.3 ± 2.9 | 1.8 ± 0.3 | 0.3 ± 0.1 | 0.8 ± 0.3 | 2.9 ± 0.7 |
| 8 | 16 | 90.3 ± | 63.7 ± 7.0 | 23.3 ± 3.4 | 3.1 ± 0.9 | 0.3 ± 0.1 | 0.1 ± 0.1 | 3.4 ± 0.9 |

[a]Mean ± SE
[b]Small foci: 1–3 crypts; Medium foci: 4–6 crypts; Large foci: 7-9 crypts; Extra large foci: ≧10 crypts; ACF >7: >7 crypts
[c]Group 1: Normal Calcium control group (5000 ppm Ca); Group 2: Low Calcium control group (2500 ppm Ca); Group 3: Supplemental Calcium group (7500 ppm Ca); Group 4: 0.02 µg 1α,25(OH)$_2$D$_3$, and 7500 ppm Ca; Group 5: 300 ppm acetylsalicylic acid and 7500 ppm Ca; Group 6: 0.02 µg 1α,25(OH)$_2$D$_3$, 300 ppm acetylsalicylic acid, and 7500 ppm Ca; Group 7: 0.02 µg 1α,25(OH)$_2$D$_3$, 300 ppm acetylsalicylic acid, and 5000 ppm Ca; Group 8: 0.02 µg 1α,25(OH)$_2$D$_3$, 300 ppm acetylsalicylic acid, and 2500 ppm Ca When comparing the high-risk group (ACF>7) on the low calcium diet (2500 ppm) to the high-risk group treated with the three active components (group 6), a highly significant reduction in the number of colonic lesions (ACF>7) (6.1 vs. 1.8, p=0.0001) is seen.

ACF and ACF>7 were observed. This demonstrates that addition of 1α,25(OH)$_2$D$_3$ and ASA to the fodder protects against progression of small ACF in animals given suboptimal calcium (2500 ppm). When increasing calcium to a higher level (5000 ppm), an obvious trend is seen (1.8 vs.

TABLE A

General Linear Models Procedure
Least Squares Means
GROUP: ACF > 7

| | LSMEAN Number | |
|---|---|---|
| 1 | 3.20000000 | 1 |
| 2 | 6.12500000 | 2 |
| 3 | 2.37500000 | 3 |
| 4 | 2.56250000 | 4 |
| 5 | 1.93750000 | 5 |
| 6 | 1.75000000 | 6 |
| 7 | 2.93750000 | 7 |
| 8 | 3.43750000 | 8 |

Probability of LSMEAN(i) = LSMEAN(j)

| i/j | 1 | 2 | 3 | 4 | 5 | 6 | 7 | 8 |
|---|---|---|---|---|---|---|---|---|
| 1 | . | 0.0094 | 0.4579 | 0.5661 | 0.2567 | 0.1931 | 0.8131 | 0.8306 |
| 2 | 0.0094 | . | 0.0008 | 0.0014 | 0.0002 | 0.0001 | 0.0041 | 0.0151 |
| 3 | 0.4579 | 0.0008 | . | 0.8637 | 0.6888 | 0.5674 | 0.6067 | 0.3316 |
| 4 | 0.5661 | 0.0014 | 0.8637 | . | 0.5674 | 0.4574 | 0.7314 | 0.4236 |
| 5 | 0.2567 | 0.0002 | 0.6888 | 0.5674 | . | 0.8637 | 0.3607 | 0.1713 |
| 6 | 0.1931 | 0.0001 | 0.5674 | 0.4574 | 0.8637 | . | 0.2781 | 0.1242 |
| 7 | 0.8131 | 0.0041 | 0.6067 | 0.7314 | 0.3607 | 0.2781 | . | 0.6472 |
| 8 | 0.8306 | 0.0151 | 0.3316 | 0.4236 | 0.1713 | 0.1242 | 0.6472 | . |

Separate addition of Calcium, 1α,25 (OH)$_2$D$_3$ or ASA, or combinations of two, also gave significant reductions in ACF indicating a protective effect. The most pronounced effect was obtained with the combination of all 3 ingredients, suggesting an additive/synergistic effect.

When regarding low calcium diets, the increase in total number of ACF in group 8 was primarily due to an increase in small ACF. Whereas in group 2, in addition to a non statistically significant increase in small ACF (p=0.061), statistically significant increases in medium, large sized 3.2, p=0.19) supporting the anticancer effect of 1α,25 (OH)$_2$D$_3$ and ASA is recognised.

In conclusion, treatment of animals given a low calcium diet with the combination of 1α,25(OH)$_2$D$_3$, Ca, and ASA results in a statistically significant reduction in the development of pre-neoplastic colonic lesions.

Tumours

Tumour bearing rats were observed in all groups (Table 4). The presented results should be taken with caution as further histological examination is needed for final evaluation. At autopsy, some of the lesions appeared very prominent and tumour-like, reddish, elevated and one to fifthteen millimetres in diameter, whereas others lesions were less elevated and had the same colour as the mucosa. Some animals had more than one tumour often 2 to 3. Other lesions were only observed when the intestine was investigated under stereomicroscope for counting of ACF. Tumours were also observed in the small intestine of one animal of groups 1, 5, 7, and 8. In group 2, two animals carried tumours in their small intestine (not histologically examined). The highest number of tumour bearing animals and total number of tumours were seen in groups 3 and 4. Group 8 receiving the lowest level of calcium in combination with ASA and 1α,25(OH)$_2$ D$_3$ had the lowest tumour burden, followed by the group 1. When comparing the numbers of tumour bearing animals of groups 2 and 8 (both receiving calcium at the lowest level), the results indicate a protective effect of the ASA and 1α,25(OH)$_2$D$_3$ combination. A similar but less pronounced tendency is seen when comparing groups 3 and 6 (both receiving the highest level of calcium).

Tumour data indicate that the combination of 1α,25(OH)$_2$D$_3$ and ASA given to animals fed either the high or low level of calcium (group 6 and 8) tended to reduce the number of tumour bearing animals and the total number of tumours when compared to the relevant control group receiving the same level of calcium. Although the reduction is non-statistically significant, this indicates protection against progression of ACF to adenomas, especially at the low calcium level, where the highest total number of ACF was recorded but the lowest number of tumour bearing animals.

TABLE 4

Cola-rectal tumour in AOM-induced rats fed diets containing 1α, 25(OH)$_2$D$_3$, acetylsalicylic acid, and various doses of Calcium - preliminary data[a]

| Group | N | No. of tumour bearing rats | No. of rats with adenoma | No. of rats with adeno-carcinoma | Total no. of tumours |
|---|---|---|---|---|---|
| 1 | 15 | 2 | 1 | 2 | 3 |
| 2 | 16 | 6 | 4 | 4[b] | 9 |
| 3 | 16 | 9 | 8 | 3 | 15 |
| 4 | 16 | 9 | 7 | 4 | 18 |
| 5 | 16 | 6 | 4 | 3 | 8 |
| 6 | 16 | 6 | 5 | 3 | 8 |

TABLE 4-continued

Cola-rectal tumour in AOM-induced rats fed diets containing 1α, 25(OH)$_2$D$_3$, acetylsalicylic acid, and various doses of Calcium - preliminary data[a]

| Group | N | No. of tumour bearing rats | No. of rats with adenoma | No. of rats with adeno-carcinoma | Total no. of tumours |
|---|---|---|---|---|---|
| 7 | 16 | 8 | 6 | 4[b] | 14 |
| 8 | 16 | 1 | 0 | 1[b] | 1 |

[a]Group 1, control diet (5000 ppm Ca); group 2, 2500 ppm Ca in the diet; group 3, 7500 ppm Ca in the diet; group 4, 0.02 μg 1α, 25(OH)$_2$D$_3$ in the diet; group 5, 300 ppm acetyl-salicylic acid and 7500 ppm Ca in the diet, group 6, 0.02 μg 1α, 25(OH)$_2$D$_3$, 300 ppm acetylsalicylic acid, and 7500 ppm Ca in the diet; group 7, 0.02 μg 1α, 25(OH)$_2$D$_3$, 300 ppm acetylsalicylic acid, and 5000 ppm Ca in the diet; group 8, 0.02 μg 1α, 25(OH)$_2$D$_3$, 300 ppm acetylsalicylic acid, and 2500 ppm Ca in the diet.
[b]including mucinous adenocarcinoma and signet-ring carcinoma.

EXAMPLE 2

The in vivo study of the effect on prevention of CRC in AOM (Azoxymethane) induced rats The rats are induced s.c 1× week in 2 weeks with an AOM solution.

The effect of the specific treatment is evaluated due to the number of aberrant crypt foci (ACF) of the colon/rectum in the AOM-induced rats. The aberrant crypt score is evaluated by stereomicroscopy (40×) upon staining with Giemsa-solution (6 ml conc. Giemsa in 50 ml of PBS, pH 7.1). The crypt size is categorised as small, medium, large and X-large. The number of animals is 80 with 16 in each group. The medicaments are administered with the food. The section is 18 weeks from the first dosage. The Ca in the food is 5000/10000 ppm, the 1,24 DHC is 2.5 microg/kg. Data for weight, food and water are registered and analysed Treatment:

Group 1. Control animals

Group 2. 200 ppm aspirin (acetylsalicylic acid)

Group 3. Ca and 1,25 DHC

Group 4. 200 ppm aspirin, Ca and 1,25 DHC

Group 5. 100 ppm aspirin, Ca and 1,25 DHC

TABLE 1

| | Small | Medium | Large | X-Large | Small | Large | Total |
|---|---|---|---|---|---|---|---|
| Control | 25 | 3 | 0 | 0 | 28 | 0 | 28 |
| Group 1 | 27 | 29 | 4 | 0 | 56 | 4 | 60 |
| | 34 | 15 | 1 | 0 | 49 | 1 | 50 |
| | 46 | 32 | 4 | 0 | 78 | 4 | 82 |
| | 16 | 21 | 1 | 0 | 37 | 1 | 38 |
| | 31 | 25 | 2 | 1 | 56 | 3 | 59 |
| | 55 | 42 | 7 | 1 | 97 | 8 | 105 |
| | 30 | 16 | 2 | 0 | 46 | 2 | 48 |
| | 99 | 61 | 4 | 0 | 160 | 4 | 164 |
| | 69 | 59 | 11 | 1 | 128 | 12 | 140 |
| | 53 | 32 | 1 | 0 | 85 | 1 | 86 |
| | 58 | 42 | 9 | 2 | 100 | 11 | 111 |
| | 40 | 26 | 9 | 2 | 66 | 11 | 77 |
| | 68 | 54 | 8 | 0 | 122 | 8 | 130 |
| | 67 | 49 | 3 | 0 | 116 | 3 | 119 |
| | 60 | 36 | 4 | 0 | 96 | 4 | 100 |
| Mean | 48.63 | 33.88 | 4.38 | 0.44 | 82.50 | 4.81 | 87.31 |
| Asp 200 | 92 | 74 | 13 | 2 | 166 | 15 | 181 |
| Group 2 | 87 | 45 | 8 | 1 | 132 | 9 | 141 |
| | 20 | 8 | 2 | 0 | 28 | 2 | 30 |
| | 51 | 34 | 5 | 3 | 85 | 8 | 93 |

TABLE 1-continued

|  | Small | Medium | Large | X-Large | Small | Large | Total |
|---|---|---|---|---|---|---|---|
|  | 31 | 10 | 2 | 0 | 41 | 2 | 43 |
|  | 82 | 51 | 5 | 0 | 133 | 5 | 138 |
|  | 73 | 35 | 3 | 0 | 108 | 3 | 111 |
|  | 44 | 31 | 3 | 0 | 75 | 3 | 78 |
|  | 55 | 22 | 3 | 0 | 77 | 3 | 80 |
|  | 47 | 49 | 5 | 1 | 96 | 6 | 102 |
|  | 40 | 21 | 1 | 0 | 61 | 1 | 62 |
|  | 22 | 9 | 2 | 0 | 31 | 2 | 33 |
|  | 46 | 26 | 6 | 1 | 72 | 7 | 79 |
|  | 73 | 47 | 5 | 0 | 120 | 5 | 125 |
|  | 44 | 18 | 4 | 0 | 62 | 4 | 66 |
|  | 63 | 50 | 1 | 0 | 113 | 1 | 114 |
| Mean | 54.38 | 33.13 | 4.25 | 0.50 | 87.50 | 4.75 | 92.25 |
| F-Test | 0.9237 | 0.660965 | 0.6512 | 0.4327 | 0.8267 | 0.7820 | 0.8051 |
| T-test | 62 | 0.452385 | 26 | 93 | 73 | 59 | 88 |
| (mean) | 0.2313 |  | 0.4566 | 0.4149 | 0.3569 | 0.4816 | 0.3665 |
|  | 06 |  | 34 | 29 | 96 | 08 | 36 |
| D3 + Ca | 41 | 37 | 4 | 1 | 78 | 5 | 83 |
| Group 3 | 31 | 43 | 1 | 0 | 74 | 1 | 75 |
|  | 53 | 37 | 4 | 0 | 90 | 4 | 94 |
|  | 35 | 7 | 2 | 0 | 42 | 2 | 44 |
|  | 89 | 57 | 2 | 0 | 146 | 2 | 148 |
|  | 88 | 52 | 5 | 1 | 140 | 6 | 146 |
|  | 25 | 12 | 1 | 0 | 37 | 1 | 38 |
|  | 26 | 13 | 0 | 0 | 39 | 0 | 39 |
|  | 65 | 29 | 1 | 0 | 94 | 1 | 95 |
|  | 53 | 30 | 3 | 0 | 83 | 3 | 86 |
|  | 42 | 36 | 2 | 0 | 78 | 2 | 80 |
|  | 52 | 49 | 3 | 0 | 101 | 3 | 104 |
|  | 32 | 26 | 1 | 0 | 58 | 1 | 59 |
|  | 36 | 19 | 2 | 0 | 55 | 2 | 57 |
|  | 25 | 6 | 0 | 0 | 31 | 0 | 31 |
|  | 30 | 17 | 0 | 0 | 47 | 0 | 47 |
| Mean | 45.19 | 29.38 | 1.94 | 0.13 | 74.56 | 2.06 | 76.63 |
| F-Test | 0.8483 | 0.921093 | 0.0035 | 0.0057 | 0.7807 | 0.0036 | 0.7155 |
| (Var) | 89 | 0.220913 | 71 | 84 | 25 | 53 | 55 |
| T-test | 0.3238 |  | 0.0081 | 0.0672 | 0.2681 | 0.0093 | 0.2132 |
| (mean) | 2 |  | 45 | 87 | 6 | 82 | 05 |
| Asp 200 | 101 | 62 | 6 | 0 | 163 | 6 | 169 |
| D3 + Ca | 71 | 58 | 8 | 0 | 129 | 8 | 137 |
| Group 4 | 31 | 21 | 0 | 0 | 52 | 0 | 52 |
|  | 79 | 60 | 2 | 0 | 139 | 2 | 141 |
|  | 64 | 26 | 3 | 0 | 90 | 3 | 93 |
|  | 52 | 42 | 2 | 0 | 94 | 2 | 96 |
|  | 56 | 23 | 3 | 0 | 79 | 3 | 82 |
|  | 41 | 25 | 1 | 0 | 66 | 1 | 67 |
|  | 88 | 44 | 3 | 0 | 132 | 3 | 135 |
|  | 64 | 25 | 1 | 0 | 89 | 1 | 90 |
|  | 61 | 29 | 1 | 0 | 90 | 1 | 91 |
|  | 40 | 11 | 1 | 0 | 51 | 1 | 52 |
|  | 37 | 46 | 8 | 1 | 83 | 9 | 92 |
| Mean | 60.38 | 36.31 | 3.00 | 0.08 | 96.69 | 3.08 | 99.77 |
| F-Test | 0.9106 | 0.957009 | 0.4073 | 0.0017 | 0.7985 | 0.2610 | 0.7580 |
| (Var) | 34 | 0.349196 | 29 | 74 | 13 | 02 | 68 |
| T-test | 0.0742 |  | 0.1169 | 0.0413 | 0.1477 | 0.0900 | 0.1900 |
| (mean) | 18 |  | 57 | 86 | 47 | 54 | 09 |
| Asp 100 | 21 | 11 | 1 | 0 | 32 | 1 | 33 |
| D3 + Ca | 57 | 20 | 5 | 0 | 77 | 5 | 82 |
| Group 5 | 62 | 72 | 16 | 2 | 134 | 18 | 152 |
|  | 67 | 52 | 1 | 1 | 119 | 2 | 121 |
|  | 34 | 48 | 2 | 0 | 82 | 2 | 84 |
|  | 31 | 44 | 18 | 4 | 75 | 22 | 97 |
|  | 53 | 39 | 5 | 0 | 92 | 5 | 97 |
|  | 36 | 16 | 0 | 0 | 52 | 0 | 52 |
|  | 16 | 7 | 2 | 0 | 23 | 2 | 25 |
|  | 44 | 19 | 4 | 0 | 63 | 4 | 67 |
|  | 41 | 29 | 3 | 0 | 70 | 3 | 73 |
|  | 33 | 39 | 10 | 2 | 72 | 12 | 84 |
|  | 69 | 20 | 0 | 0 | 89 | 0 | 89 |
|  | 34 | 16 | 3 | 0 | 50 | 3 | 53 |
|  | 18 | 20 | 1 | 0 | 38 | 1 | 39 |
|  | 26 | 10 | 0 | 0 | 36 | 0 | 36 |

TABLE 1-continued

|  | Small | Medium | Large | X-Large | Small | Large | Total |
|---|---|---|---|---|---|---|---|
| Mean | 40.13 | 28.88 | 4.44 | 0.56 | 69.00 | 5.00 | 74.00 |
| F-Test (Var) | 0.3723 2 | 0.703108 0.211847 | 0.0687 88 | 0.0845 34 | 0.4728 62 | 0.0550 55 | 0.6031 21 |
| T-test (mean) | 0.1132 69 |  | 0.4848 12 | 0.3584 15 | 0.1357 54 | 0.4614 5 | 0.1573 56 |

"Small" in the third column is the sum of small and medium of the first column

"Large" in the third column is the sum of large and x-large the of second column The risk of malignant development (APC and ras-mutations) is correlated to large and x-large crypts.

The aspirin dosage generally considered as being preventive is 400–500 ppm in AOM-induced F344 rats.

The results shows that it is not possible to reduce the aspirin dosage to 200 ppm as this dosage is without effect (Group 2). However, the addition of Ca and 1,25 DHC results in a significant reduction in large ACF (Group 4). The results of Groups 3 and 4 are peculiar as it seems as though the presence of aspirin is an adverse effect. It should be noted that the rats suffered from hypercalcaemia as shown by kidney stones.

References:
1. Trujillo M A, Garewal, H S, Sampliner R E. Non-steroidal anti-inflammatory agents in chemoprevention of colorectal cancer. At what cost? Dig Dis Sci 1994;39:2260–6.
2. Caplan L S, Hutton M, Muller D S & al. Secondary prevention of cancer. Curr Opin Oncol 1996;8:441–6.
3. Clemmesen I H, Storm H. Kraeft in Danmark. En opslagsbog. Kreftens Bekaompelse 1993.
4. Key J A K, Thorogood M, Appleby P N & al. Dietary habits and mortality in 11000 vegetarians and health conscious people: results of a 17 year follow up. BMJ 1996;313:7060
5. Raskov H. Adjuverende systemisk kemoterapi ved cancer coli. Ugeskrift for Laeger 1996;158:1222–7.
6. Garland C F, Barrett-Connor E, Ressof A H & al. Dietary vitamin D and calcium and risk of colorectal cancer: a 19-year prospective study in men. Lancet 1985; i:307–9.
7. Garland C F, Garland F C, Shaw E K & al. Serum 1,25 hydroxyvitamin D and colon cancer eight-year prospective study. Lancet 1989; nov 18:1176–8.
8. Garland C F, Garland F C, Gorham E D. Can colon cancer incidence and death rates be reduced with calcium and vitamin D? Am J Clin Nutr 1991;54:193S-201S.
9. Kune G A, Kune S, Watson L F. Colorectal cancer risk, chronic illnesses, operations and medications: case control results from the Melbourne Colorectal Cancer Study. Cancer Res 1988;48:4399–404.
10. Suh O, Mettlin C, Petrelli N J. Aspirin use, cancer and polyps of the large bowel. Cancer 1993;72:1171–7.
11. Thun M J, Namboodiri M M, Heath C W Jr. Aspirin use and reduced risk of fatal colon cancer. N Engl J Med 1991;325:1593–6.
12. Buring J E, Lee I M, Hennekens C H. Non-steroidal inflammatory drugs and colorectal cancer. Cancer 1994;74:1837–9.
13. Heath C W, Thun M J, Greenberg E R & al. NSAID and human cancer. Cancer 1994;74:2885–8.
14. Pence B C. Role of calcium in colon cancer prevention: experimental and clinical studies. Mut Res 1993;290:87–95.
15. Duris I, Hruby D, Pekarkova B, Huorka M, Cernakova E, Bezayova T & al. Calcium chemoprevention in colorectal cancer. Hepatogastroenterol 1996;43:152–4.
16. Buset M, Winaver M L S, Swaroop S, Friedmann E. Inhibition of human colonic epithelial cell proliferation in vivo and in vitro by calcium. Cancer Res 1986;46:5426–30.
17. Wargovich M J, Lointier P H. Calcium and vitamin D modulate mouse colon epithelial proliferation and growth characteristics of a human colon tumour cell line. Can J Physiol Pharmacol 1987;65:472–7
18. IARC Handbooks of Cancer Prevention, vol 1. Non-steroidal anti-inflammatory drugs. Lyons: International Agency for Research on Cancer. In Press.
19. Dorudi S, Hanby A M, Poulsom R, Northover J, Hart I R. Levels of expression of E-cadherin m-RNA in colorectal cancer correlates with clinical outcome. Br J Cancer 1995;71:614–6.
20. Newmark H L, Lipkin M. Calcium, vitamin D and colon cancer. Cancer Research 1992;52:2067S-70S.
21. Rasmussen H. The calcium messenger system. N Engl J Med 1986;314:1094–1101.
22. Llor X, Jacoby R F, Teng B B, Davidson N O, Sitrin M D, Brasitus T A K-ras mutations in 1,2 dimethylhydrazine induced colonic tumours: effects of supplemental dietary calcium and vitamin D deficiency. Cancer Res 1991;51:4305–9.
23. Reshef R Rozen P, Fereman Z, Fine N, Barzilai M, Sasha S M, Shkolnik T. Effect of a calcium enriched diet on the colonic epithelium hyperproliferation induced by N-methyl-N-nitro-N-nitrosoguanidine in rats on a low calcium and fat diet. Cancer Res 1990;50:1764–7.
24. Kane K F, Mitchell N P, Langman M J S & al. Functional vitamin $D_3$ receptors are present in human colorectal neoplasms. Gastroenterology 1995; 108:A487.
25. Anticancer Res 1996;16:2333–8.
26. Eisman J A, Barkla D H, Tutton P J M. Suppression of in vivo growth of human cancer solid xenografts by 1,25dihydroxyvitamin $D_3$. Cancer Res 1987;47:21–5.
27. Newmark H L, Lipkin M. Calcium, Vitamin D and Colon Cancer. Cancer Res 1992;52s:2067s-70s.
28. Newmark H L, Lipkin M. Calcium, Vitamin D and Colon Cancer. Cancer Res 1992;52s:2067s-70s.
29. Tement C, Ding X Z, Adrian T. Lipoxygenase blockade inhibits growth factor-induced colonic cancer cell proliferation. Abstract, ASCRS Ann Meeting 1999, Washington DC.

30. Marcus A J. Aspirin as prophylaxis against colorectal cancer. N Engl J Med 1995;333:656–8.
31. Frolich J C. A classification of NSAIDs according to the relative inhibition of cyclooxygenase enzymes. TIPS 1997;18:30–4.
32. Hanif A P, Feng Y, Koutsos M & al. NSAIDs inhibit the growth of colon cancer cell lines by a prostaglandin independent pathway. Gastroenterology 1995;108: A478.
33. Ahnen D, Piazza G, Alberts D & al. Sulindac sulfide and sulfone both inhibit the growth of colon cancer cell lines by inducing apoptosis. Gastroenterology 1995;;108: A443.
34. Alberts D S, Hixson L J, Ahnen D, Bogert C, Einspahr J, Paranka N & al. Do NSAIDs exert their colon cancer chemoprevention activities through the inhibition of mucosal prostaglandin synthetase? J Cell Biochem 1995; s22:18–23.
35. Kahlenberg M, Stoler D, Volpe C, Petrelli N, Anderson G. Nonsteroidal anti-inflammatory drugs (NSAID's) reduce genomic instability in colorectal tumour cells. Abstract. Surgical Oncology Societies 51st annual cancer symposium 1998.
36. Levy G. Prostaglandin H synthases, nonsteroidal anti-inflammatory drugs and colon cancer. FASEB J 1997;11:234–47.
37. Hixson L J, Alberts D S, Krutzsch M, Einspahr J, Brendel K, Gross PH & al. Antiproliferative effect of nonsteroidal anti-inflammatory drugs against human colon cancer cells. Cancer Epidemiol Biomarkers Prev 1994;3:5 433–8.
38. Dubois R N, Giardello F M, Smalley W E. Nonsteroidal anti-nflammatory drugs, eicosanoids and colorectal cancer prevention. Gastroenterol Clin N Am 1996;25:773–91.
39. Watson A J. Chemopreventive effects of NSAIDs against colorectal cancer: regulation of apoptosis and mitosis by COX-1 and COX-2. Histol Histopathol 1998;13:591–7.
40. Steering Committee of the Physicians Health Study Research Group. Final report on the aspirin component of the ongoing Physician Health Study. N Engl J Med 1989;321:129–35.
41. Muscat J E, Stellman S D, Wynder E L. NSAID and colorectal cancer Cancer 1994;74:1847–54.
42. Giovannucci E, Egan K M, Hunter D J & al. Aspirin and the risk of colorectal cancer. N Engl J Med 1995;333:609–14.
43. Giovannucci E, Rimm E B, Stampfer M J & al. Aspirin use and the risk of colorectal cancer and adenoma in male health professionals. Ann Int Med 1994;121:241–6.
44. Pollard M, Luckert P H. Effect of indomethacin on intestinal tumours induced in rats by the acetate derivative of dimethylnitrosamine. Science 1981;214:558–9.
45. Narisawa T. Sato M, Tani M & al. Inhibition of development of methyinitrosurea induced rat colon tumours by indomethacin treatment. Cancer Res 1981;41:1954–7.
46. Reddy B S, Maruyama H, Kelloff G. Dose-related inhibition of colon carcinogenesis by dietary piroxicam, a nonsteroidal anti-inflammatory drug, during different stages of rat colon tumour development. Cancer Res 1987;47:5340–6.
47. Kudo T, Narisawa T, Abo S. Antitumour activity of indomethacin on methylazoxymethanol-induced large bowel tumours in rats. Gann;71 :260–4.
48. CAPRIE Steering Commitee. A randomised, blinded, trial of clopidogrel versus aspirin in patients at risk of aschaemic events (CAPRIE). Lancet 1996;348:1329–39.
49. Duffy M A, (ed.), Physicians' Desk Reference. Montvale, N.J. Medical Economics Data, p. 780, 1993.
50. McEvoy G K, McQuarrie G M. Aspirin. In: Drug Information 86, Bethesda, Md.: American Society of Hospital Pharmacists 1986:841–8.
51. Kristiansen, E, Thorup, I, and Meyer, O: Influence of different diets on development of DMH-induced aberrant crypt foci and colon tumour incidence in Wistar rats. *Nutr Cancer* 23, 151–159, 1995.
52. Diaz, Dario, et al.: Apoptosis is induced by the active metabolite of vitamin D3 and its analogue EB1089 in colorectal adenoma and carcinoma cells: possible implications for prevention and therapy: Cancer research 60, 2304–2312, 2000.
53. Tsujiuchi T, Tsutsumi M, Sasaki Y, Murata N, Konishi Y. Mutations of adenomatous polyposis coli and beta-catenin during progression of lung tumours induced by N-nitrosobis (2-hydroxypropyl) amine in rats. Cancer Res 2000;60:6611–6.
54. Sunaga N, Kohno T. Kolligs F T, Fearon E R, Saito R, Yokota J. Constitutive activation of the Wnt signalling pathway by CTNNB1 (beta-catenin) mutations in a subset of human lung adenocarcinoma. Genes Chromosomes Cancer 2001 ;30:316–21.
55. Piyathilake C J, Johanning G L, Macaluso M, Whiteside M, Oelschlager D K & al. Localized folate and vitamin B-12 deficiency in squamous cell lung cancer is associated with global DNA hypomethylation. Nutr Cancer 2000;37:99–107.
56. Hirsch F R, Franklin W A, Gazdar A F, Bunn P A. Early detection of lung cancer: clinical perspectives of recent advances in biology and radiology. Clin Cancer Res 2001;7:5–22.
57. Saha D, Datta P K, Sheng H, Morrow J D, Wada M & al. Synergistic induction of cyclooxygenase-2 by transforming growth factor-betal and epidermal growth factor inhibits apoptosis in epithelial cells. Neoplasia 1999;1:508–17.
58. Kim T, Mo E K, Yoo C, Lee C, Han S K, Shim Y, Kim Y W. Alteration of cell growth and morphology by overexpression of transforming growth factor beta type II receptor in human lung adenocarcinoma cells. Lung cancer 2001;31:181–91.
59. Marrogi A J, Travis W D, Welsh J A, Khan M A, Rahim H & al. Nitric oxide synthase, cyclooxygenase-2 and vascular endothelial growth factor in the angiogenesis of non-small cell lung carcinoma. Clin Cancer Res 2000;6:4739–44.
60. Hosomi Y, Yokose T, Hirose Y. Nakajima R, Nagai K & al. Increased cyclooxygenase 2 (COX-2) expression occurs frequently in precursor lesions of human adenocarcinoma lung. Lung Cancer 2000;30:73–81.
61. Shirharama T. Cyclooxygenase-2 expression is upregulated in transitional cell carcinoma and its preneoplastic lesions in the human urinary bladder. Clin Cancer Res 2000;6:2424–30.
62. Ristimaki A, Nieminen O, Saukkonen K, Hotakainen K, Nordling S, Haglund C. Expression of cyclooxygenase-2 in human transitional cell carcinoma of the urinary bladder. Am J Pathol 2001;158:849–53.

63. Rioux N, Castonguay A. The induction of cyclooxygenase-1 by a tobacco carcinogen in U937 human macrophages is correlated to the activation of NF-kappaB. Carcinogenesis 2000;21:1745–51.

64. Witschi H, Uyeminami D, Moran D, Espiritu I. Chemoprevention of tobacco-smoke lung carcinogenesis in mice after cessation of smoke exposure. Carcinogenesis 2000;21:977–82.

What is claimed is:

1. A method for the prevention of progression of colorectal cancer prevention of colorectal cancer, prevention of initiation of colorectal cancer or a combination thereof in a human comprising administering to the human in need thereof a synergistically-effective amount of a combination dosage, which comprises acetylsalicylic acid (ASA), a vitamin $D_3$, metabolite 1,25 dihydroxy-cholecalciferol (1,25 DHC) and calcium and a pharmaceutically acceptable carrier.

2. A method according to claim 1 wherein the acetylsalicylic acid (ASA) is included in the range of 50 mg to 500 mg.

3. A method according to claim 1 wherein calcium is included in the range of 200 mg to 3000 mg.

4. A method according to claim 1 wherein the human comprises a human in risk of development of colorectal cancer due to being a first-degree relative to a patient with colorectal cancer, a human who carries the gene(s) for hereditary non-polyposis colorectal cancer (HNPCC), a human having familial adenomatous polyposis, colorectal adenomas, or a human having an inflammatory bowel disease.

5. A method according to claim 1 wherein the human, during or prior to the administration of the combination dosage, receives treatment for *Helicobacter pylori*.

6. A method according to claim 4, wherein the inflammatory bowel disease is ulcerative colitis or Crohns disease.

7. A method according to claim 1 wherein the combination dosage consists essentially of ASA, 1,25 DHC, calcium and a pharmaceutically acceptable carrier.

8. A method according to claim 1 wherein the combination dosage comprises 50 to 75 mg ASA, 500 to 1000 mg of calcium, and 0.5 $\mu$g to 1 $\mu$g of 1,25 DHC or 0.02 to 2 $\mu$g 1.25 DHC.

9. A pharmaceutical medicament comprising a synergistically-effective amount of a combination dosage which comprises ASA, 1,25 DHC, calcium and a pharmaceutically acceptable carrier.

10. A pharmaceutical medicament according to claim 9 wherein the combination dosage comprises 1,25 DHC in the range of 0.02 $\mu$g to 2 $\mu$g.

11. A pharmaceutical medicament according to claim 9 or 10 wherein the combination dosage comprises calcium in the range of 200 mg to 3000 mg.

12. A pharmaceutical medicament according to claim 9 wherein the combination dosage comprises ASA in the range of 50 mg to 500 mg.

13. A pharmaceutical medicament according to claim 9 wherein the combination dosage comprises 50 to 75 mg ASA, 500 to 1000 mg of calcium, and 0.5 $\mu$g to 1 $\mu$g of 1,25 DHC.

* * * * *